(12) United States Patent  
Krueger

(10) Patent No.: US 8,308,804 B2
(45) Date of Patent: Nov. 13, 2012

(54) SPINAL FUSION DEVICE

(76) Inventor: David Krueger, Austin, TX (US)

( * ) Notice: Subject to any disclaimer, the term of this patent is extended or adjusted under 35 U.S.C. 154(b) by 420 days.

(21) Appl. No.: 12/618,930

(22) Filed: Nov. 16, 2009

(65) Prior Publication Data

US 2010/0125334 A1  May 20, 2010

Related U.S. Application Data

(60) Provisional application No. 61/114,636, filed on Nov. 14, 2008.

(51) Int. Cl.
*A61F 2/44* (2006.01)

(52) U.S. Cl. .................................. 623/17.16; 623/17.11

(58) Field of Classification Search ...... 623/17.11–17.16
See application file for complete search history.

(56) References Cited

U.S. PATENT DOCUMENTS

| | | | |
|---|---|---|---|
| 5,397,364 A | 3/1995 | Kozak | |
| 6,045,579 A | 4/2000 | Hochshuler | |
| 6,080,193 A | 6/2000 | Hochshuler | |
| 6,576,016 B1 | 6/2003 | Hochshuler | |
| 6,648,917 B2 | 11/2003 | Gerbec | |
| 6,755,841 B2 | 6/2004 | Fraser | |
| 6,852,129 B2 | 2/2005 | Gerbec | |
| 7,326,250 B2 | 2/2008 | Beaurain | |
| 7,749,255 B2 | 7/2010 | Johnson et al. | |
| 7,967,867 B2 | 6/2011 | Barreiro et al. | |
| 2003/0233145 A1 | 12/2003 | Landry | |
| 2004/0002758 A1 | 1/2004 | Landry | |
| 2004/0030387 A1 | 2/2004 | Landry | |
| 2005/0060034 A1* | 3/2005 | Berry et al. | 623/17.11 |
| 2005/0197702 A1* | 9/2005 | Coppes et al. | 623/17.12 |
| 2006/0015183 A1 | 1/2006 | Gilbert | |
| 2007/0250173 A1 | 10/2007 | Berry | |
| 2007/0270968 A1 | 11/2007 | Baynham | |

* cited by examiner

*Primary Examiner* — Andrew Yang
*Assistant Examiner* — Olivia C Chang
(74) *Attorney, Agent, or Firm* — Michael X. Ye; Andrews Kurth, LLP

(57) ABSTRACT

A spinal fusion device is disclosed. The spinal fusion device includes a first endplate configured for fitting within a disc space and engaging with a first vertebra and a second endplate configured for fitting within the disc space and engaging with a second vertebra. The two endplates are separated by a single spacer that is positioned between the first endplate and the second endplate and maintains a pre-determined distance between the first endplate and the second endplate. The spacer contains an anterior end, a posterior end, a first lateral side, a second lateral side opposite to the first lateral side, a first surface that engages with the first endplate, a second surface that engages with the second endplate. Also disclosed are methods and instruments for implanting the spinal fusion device.

20 Claims, 20 Drawing Sheets

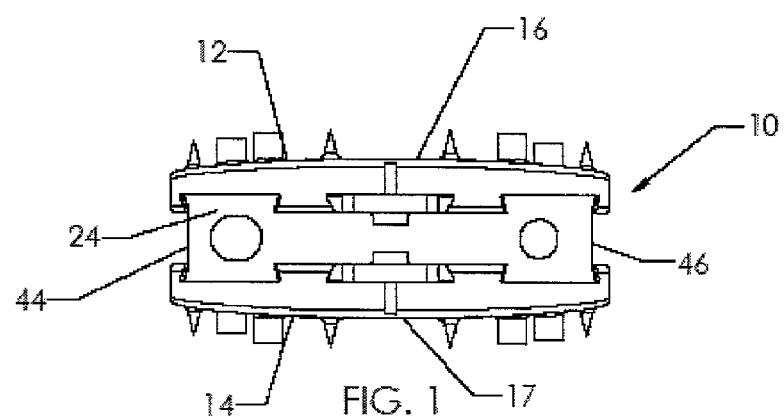
FIG. 1
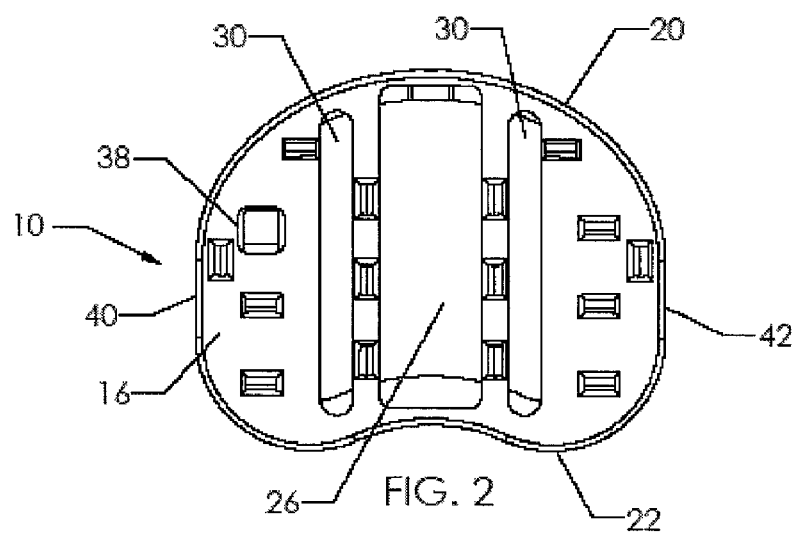
FIG. 2
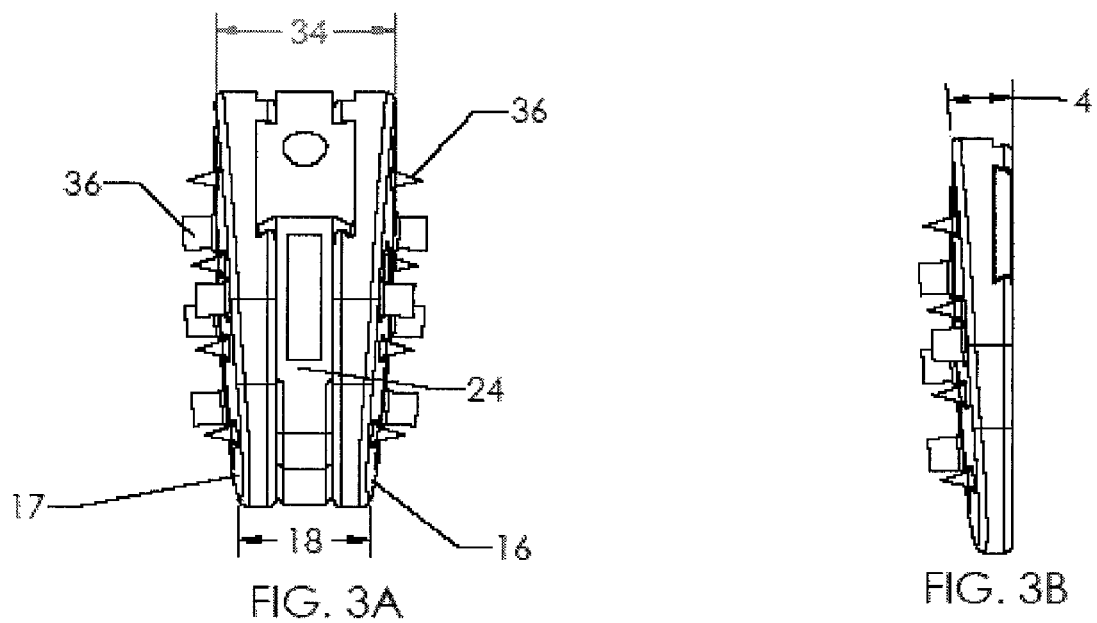
FIG. 3A
FIG. 3B

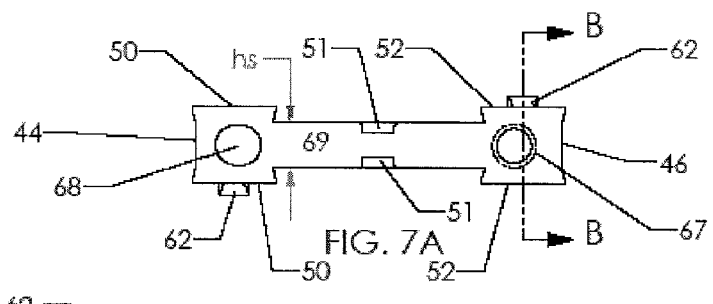
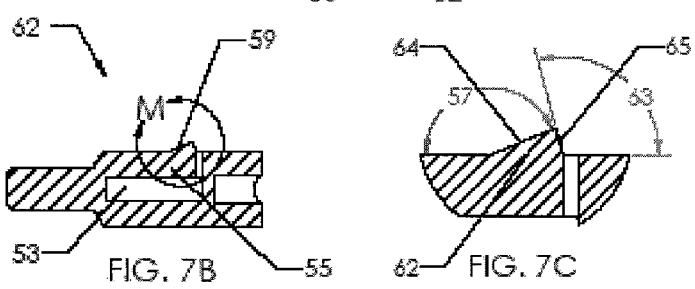
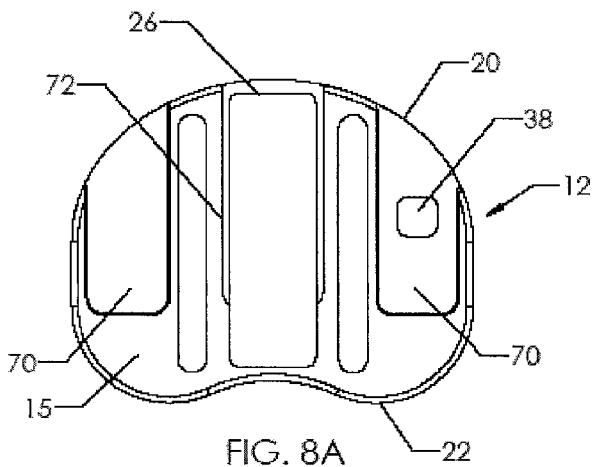
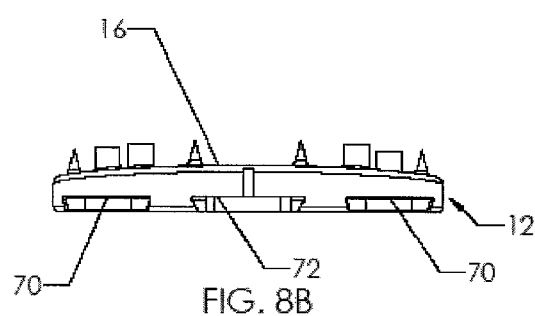

```
┌─────────────────────────────────────────────────────────────────────┐
│ Preparing a spinal disc space between two adjacent vertebrae by     │
│ removing the intervertebral disc along with anterior osteophytes    │
│ adjacent to the interspace                                          │
│                                                                2102 │
└─────────────────────────────────────────────────────────────────────┘
                                  ▼
┌─────────────────────────────────────────────────────────────────────┐
│ Determining the appropriate size endplate footprint using a thin    │
│ endplate trial                                                      │
│                                                                2104 │
└─────────────────────────────────────────────────────────────────────┘
                                  ▼
┌─────────────────────────────────────────────────────────────────────┐
│ Determining the appropriately sized implant using an implant        │
│ construct trial                                                     │
│                                                                2106 │
└─────────────────────────────────────────────────────────────────────┘
                                  ▼
┌─────────────────────────────────────────────────────────────────────┐
│ Coupling an endplate inserter with a pair of endplates              │
│                                                                2108 │
└─────────────────────────────────────────────────────────────────────┘
                                  ▼
┌─────────────────────────────────────────────────────────────────────┐
│ Inserting the endplates into the spinal disc space                  │
│                                                                2110 │
└─────────────────────────────────────────────────────────────────────┘
                                  ▼
┌─────────────────────────────────────────────────────────────────────┐
│ Coupling a spacer inserter with a spacer                            │
│                                                                2112 │
└─────────────────────────────────────────────────────────────────────┘
                                  ▼
┌─────────────────────────────────────────────────────────────────────┐
│ Inserting the spacer inserter with the spacer into a lumen of the   │
│ endplate inserter                                                   │
│                                                                2114 │
└─────────────────────────────────────────────────────────────────────┘
                                  ▼
┌─────────────────────────────────────────────────────────────────────┐
│ Advancing the spacer towards the posterior end of the endplates     │
│ until the lock tabs on the spacer lock into the corresponding lock  │
│ slots on the endplates                                              │
│                                                                2116 │
└─────────────────────────────────────────────────────────────────────┘
                                  ▼
┌─────────────────────────────────────────────────────────────────────┐
│ Decoupling the spacer inserter from the spacer                      │
│                                                                2118 │
└─────────────────────────────────────────────────────────────────────┘
                                  ▼
┌─────────────────────────────────────────────────────────────────────┐
│ Decoupling the endplate inserter from the endplates                 │
│                                                                2120 │
└─────────────────────────────────────────────────────────────────────┘
```

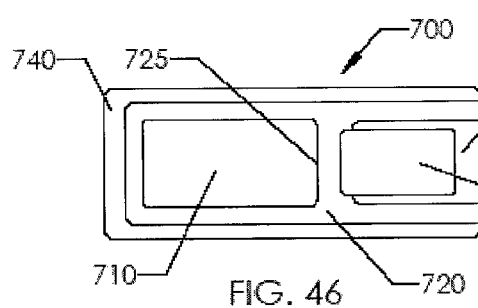
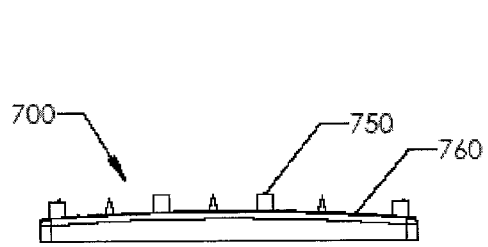
FIG. 46  FIG. 47
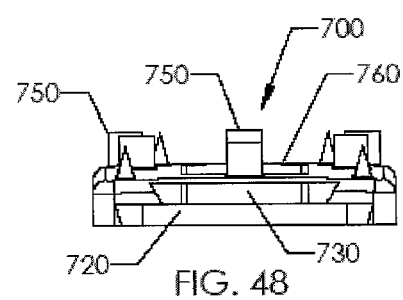
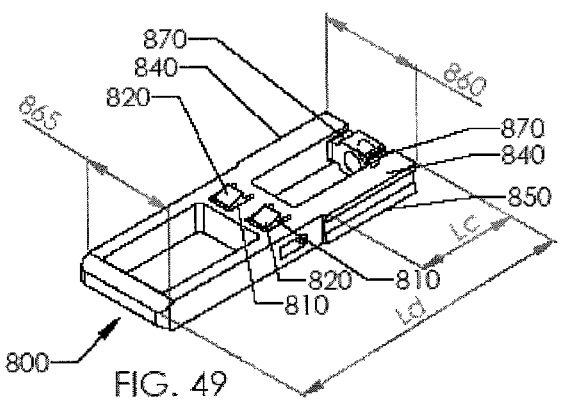
FIG. 48  FIG. 49
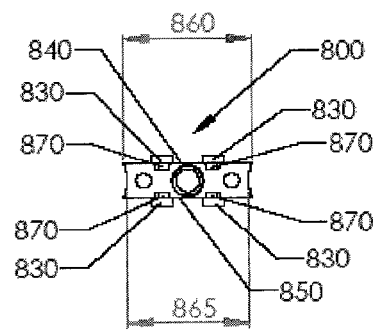
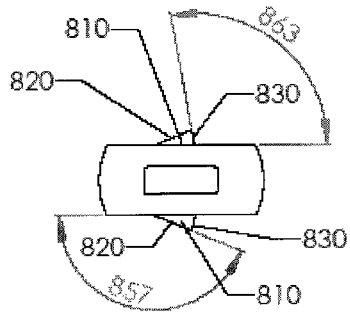
FIG. 50A  FIG. 50B
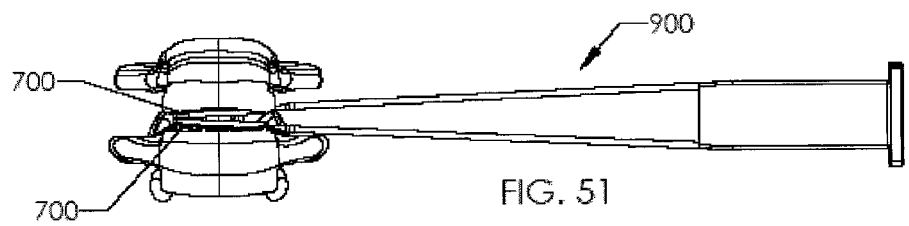
FIG. 51

SPINAL FUSION DEVICE

RELEVANT APPLICATIONS

This application claims priority of U.S. Provisional Application Ser. No. 61/114,636, filed on Nov. 14, 2008, which is hereby incorporated in its entirety.

TECHNICAL FIELD

The technical field is medical devices and, more particularly, spinal fusion devices.

BACKGROUND

The vertebral column, or the spinal column, is composed of a series of connected bones called "vertebrae." The vertebrae surround the spinal cord and protect the spinal cord from damage. Nerves branch off the spinal cord and travel to the rest of the body, allowing for communication between the brain and the body. The vertebrae are connected by spongy intervertebral discs. The intervertebral disc, which is made up of strong connective tissues that hold one vertebra to the next, acts as a cushion or shock absorber between the vertebrae.

Spinal fusion is a surgical procedure used to correct problems with the vertebrae and/or intervertebral disc, such as degenerative disc disease, spinal disc herniation, discogenic pain, weak or unstable spine caused by infections or tumors, vertebral fracture, scoliosis, kyphosis, spondylolisthesis, spondylosis, Posterior Rami Syndrome, and other degenerative spinal conditions that causes instability of the spine.

In a typical spinal fusion procedure, the intervertebral disc is partially or fully removed. Although a number of spinal fusion devices have been developed, there still exists a need for a spinal fusion device that is capable of maintaining the height and the natural lordosis of the spine, and that can easily be assembled and dissembled in a surgical procedure.

SUMMARY

A spinal fusion device is disclosed. The spinal fusion device includes a first endplate having a first endplate that has an anterior end and a posterior end and is configured for fitting within a disc space and engaging with a first vertebra, and a second endplate that has an anterior end and a posterior end and is configured for fitting within the disc space and engaging with a second vertebra. The endplates are separated by a single spacer that maintains a pre-determined distance between the endplates. The spacer contains an anterior end, a posterior end, a first lateral side, a second lateral side opposite to the first lateral side, a first surface that engages with the first endplate, a second surface that is opposite to the first surface and engages with the second endplate, and locking means that releasably engages with the first and second endplates and allows in situ disassembly of the spacer from the fusion device after implantation.

Also disclosed is a spinal fusion device that includes a first endplate that has an anterior end and a posterior end and is configured for fitting within a disc space and engaging with a first vertebra, and a second endplate that has an anterior end and a posterior end and is configured for fitting within the disc space and engaging with a second vertebra. The endplates are separated by a single spacer that maintains a pre-determined distance between the endplates. The spacer includes an anterior end, a posterior end, a first lateral side, a second lateral side opposite to the first lateral side, a first surface that engages with the first endplate, a second surface that is opposite to the first surface and engages with the second endplate. At least one of the first and the second endplates is locked to the spacer by engaging a flexible tab into a locking slot.

Also disclosed is a method for implanting the spinal fusion device in a subject. The method includes preparing a disc space between two adjacent vertebrae, inserting a pair of endplates into the disc space, wherein each endplate comprises an anterior end, a posterior end, a locking hole, and spikes on an outer surface, inserting a spacer between the pair of endplates, and advancing the spacer between the pair of endplates towards the posterior end of the endplates until locking tabs on the spacer engage with corresponding locking holes on the first and second endplates. The spacer includes an anterior end, a posterior end, a first surface that engages with the first endplate, a second surface that engages with the second endplate, a first flexible locking tab on the first surface, and a second flexible locking tab on the second surface.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein corresponding reference characters indicate corresponding parts throughout the several views and wherein:

FIG. 1 is a front view of an embodiment of a spinal fusion device;

FIG. 2 is a top view of the spinal fusion device of FIG. 1;

FIG. 3A is a side view of the spinal fusion device of FIG. 1;

FIG. 3B is a side view of an endplate of the spinal fusion device 1;

FIG. 7A is a front view of the spacer of FIG. 5;

FIG. 7B is cross sectional view of the spacer of FIG. 5 taken along line B-B of FIG. 7A;

FIG. 7C is an enlarged cross sectional view of the flexible tab of FIG. 7B;

FIG. 8A is plan view of the inner surface of an endplate of the spinal fusion device of FIG. 1;

FIG. 8B is a front view of the endplate of FIG. 8A;

FIG. 21 is a flow chart showing an embodiment of a method for implanting the spinal fusion device.

FIG. 46 is plan view of the inner surface of an endplate of the spinal fusion device of FIG. 44A;

FIG. 47 is a front view of an endplate of the spinal fusion device of FIG. 44A;

FIG. 48 is a side view of an endplate of the spinal fusion device of FIG. 44A;

FIG. 49 is a perspective view of a spacer of the spinal fusion device of FIG. 44A;

FIG. 50A is a side view of a spacer of the spinal fusion device of FIG. 44A;

FIG. 50B is an enlarged view of the flexible tabs of FIG. 49;

FIG. 51 is a side view of the endplate inserter coupled with the endplates being inserted in between the adjacent vertebrae using a lateral approach;

DETAILED DESCRIPTION

Figure 4A:
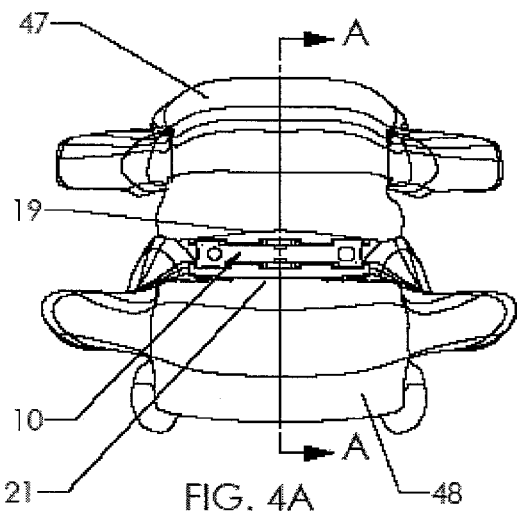
FIG. 4A is a front view of adjacent vertebral bodies with the spinal fusion device of FIG. 1 disposed therebetween.

In the following detailed description, reference is made to the accompanying drawings which form a part hereof wherein like numerals designate like parts throughout, and in which is shown by way of illustration embodiments in which the invention may be practiced. It is to be understood that other embodiments may be utilized and structural or logical changes may be made in alternate embodiments. Therefore, the following detailed description is not to be taken in a limiting sense, and the scope of embodiments in accordance with the present invention is defined by the appended claims and their equivalents.

This description is intended to be read in connection with the accompanying drawings, which are to be considered part of the entire written description of this invention. The drawing figures are not necessarily to scale and certain features of the invention may be shown exaggerated in scale or in somewhat schematic form in the interest of clarity and conciseness. In the description, relative terms such as "horizontal," "vertical," "up," "down," "top," "bottom," "outer," "inner," "front," "back," "anterior," and "posterior," as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "upwardly" versus "downwardly," "longitudinal" versus "lateral" and the like are to be interpreted relative to one another or relative to an axis of elongation, or an axis or center of rotation, as appropriate. Terms concerning attachments, coupling and the like, such as "connected" "interconnected," "coupled," "engaged" and "attached" refer to a relationship wherein structures are secured or attached to one another either directly or indirectly through intervening structures, as well as both movable or rigid attachments or relationships, unless expressly described otherwise. The term "operatively connected" is such an attachment, coupling or connection that allows the pertinent structures to operate as intended by virtue of that relationship.

Embodiments of a spinal fusion device that provides column support to the spine and facilitates a fusion between adjacent vertebral bodies are disclosed. In certain embodiments, the fusion device includes three pieces, namely, a pair of endplates configured to be attached to vertebrae flanking a vertebral disc space, and a single spacer positioned between the two endplates and releasably attached to the two endplates to maintain the endplates in a lordotic alignment.

In an embodiment, the endplates of the fusion device are shaped to match the general shape of the vertebral body and to inhibit subsidence into the vertebra. The outer faces of the pair of endplates contain projections that extend into and engage with the end of vertebrae. The projections reduce migration of the device within the disc space after engagement with the end of vertebrae. The endplates include a variety of openings to allow bone to grow through the endplates. The endplates may include one or more slots with a dovetail-shaped cross section. The one or more slots extend from the anterior end of the endplates to the posterior end of the endplate, and are sized to receive the corresponding sliding plate or plates of the spacer. As used hereinafter, the "anterior end" of an end plate is the end from which the spacer is inserted between two endplates.

In this embodiment, the spacer has a shape that generally matches the shape of the mating endplates. The spacer has two arms connected by a crossing bar at the posterior ends or at both the posterior ends and anterior ends. The spacer is used to distract the endplates during insertion and is always inserted between the two endplates in an anterior-to-posterior direction.

In an embodiment, the spacer contains one or more flexible tabs that interface with corresponding slots on the engaging endplates to lock the spacer to the endplates. The flexible tab/slot design allows the spacer to be locked into the endplates without the use of locking instrumentation. In another embodiment, each endplate contains one or more flexible tabs that interface with corresponding slots on the surface of the spacer to lock the endplate to the spacer.

In an embodiment, the flexible tab also contains a sloped sidewall that allows the spacer to be disengaged from the endplates by pulling the spacer with sufficient force in the posterior-to-anterior direction, so as to dissemble an implanted fusion device in situ.

The top and the bottom surface of the two arms of the spacer may contain dovetail-shaped sliding plates to interface with the corresponding slots on the endplates. During the assembling process, the spacer is inserted between the pair of endplates in the anterior-to-posterior direction. Once fully engaged with the endplates, the single piece spacer provides support to endplates along lateral, anterior, and posterior aspects of the fusion device to share axial compressive loads. In one embodiment, the spacer includes an opening proximate the anterior end for placing the bone graft after it has been assembled within the intervertebral space.

In an embodiment, the top and bottom surfaces of the spacer are substantially parallel to each other, so as to separate the endplates from each other in a parallel fashion. A lordotic angle is created through various angles created in the engaging endplates.

In an embodiment, the height of the spacer is designed to vary along the length in the anterior-posterior direction, such that the height between the anterior end of the spacer is greater than the height between the posterior end of the spacer. In this embodiment, the lordotic angle is created by the spacer and not through various angles created in the engaging endplates.

In an embodiment, the lordotic angle is created by both the endplate and the spacer. The modular design of the spinal fusion device allows for the device to be customized to fit a particular patient's anatomy. The spinal fusion device can be used in the lumbar spine and in the cervical spine as well.

FIGS. 1-9 show embodiments of a spinal fusion device 10. As shown in FIGS. 1 and 2, the assembled device 10 has an anterior end 20, a posterior end 22 and two sides 40 and 42. The device 10 generally includes endplates 12 and 14 and a spacer 24 sandwiched between the endplates 12 and 14. The outer surfaces 16 and 17 of the endplates 12 and 14 are shaped similar to the natural shape of the vertebral body to provide a relatively large contact area between the endplates and the interfacing vertebral bodies. The contact force between the vertebrae and the endplates is imparted over a large surface area and hence reduces the risk of subsidence of the fusion device 10 into the vertebrae. In this embodiment, the outer surface 16 or 17 of endplates 12 or 14, respectively, has a slightly convex shape to conform to the concave end surfaces 19 and 21 of vertebrae 47 and 48, as shown in FIG. 4B. As shown in FIG. 2, the outer surfaces 16 and 17 of the endplates 12 and 14 may contain a variety of openings 26 and 30 to allow bone growth through the endplates 12 and 14 and between the adjacent vertebrae 47 and 48 shown in FIGS. 4A and 4B.

Figure 4B:
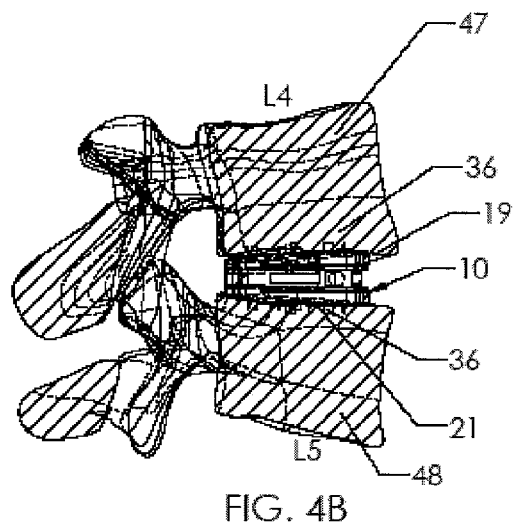
FIG. 4B is a cross sectional view of the adjacent vertebral bodies and the spinal fusion device of FIG. 1 taken along line A-A of FIG. 4A.

Referring now to FIG. 3A, the outer surfaces 16 and 17 of the endplates 12 and 14 may contain multiple spikes 36 protruding from the outer surfaces 16 and 17 to anchor the endplates 12 and 14 to the end surface 19 and 21 of corresponding vertebrae 47 and 48 (see FIG. 4B). The spikes 36 extend into the body of vertebrae 47 and 48 to prevent migration of the fusion device 10 within the disc space after implantation. The spacer 24 is engaged with both endplates 12 and 14 and maintains the distance between two endplates. Spacers of different thickness may be used to create spinal fusion devices with desired height (i.e., a height that matches the height of the disc space in which the spinal fusion device is implanted).

In order to maintain the natural lordotic angle of the spine, the thickness of the spinal fusion device 10 may vary from the anterior end 20 to the posterior end 22. As shown in FIG. 3A, the spinal fusion device 10 has a posterior height 18 defined by the distance between the outer surfaces 16 and 17 at the posterior end 22 of the endplates 12 and 14, and an anterior height 34 defined by the distance between the outer faces 16 and 17 at the anterior end 20 of the endplates 12 and 14. The anterior height 34 is greater than the posterior height 18 in order to maintain the natural lordotic angle of the spine. In this embodiment, the different heights at the anterior end and the posterior end is achieved by varying the thickness of the endplates 12, 14 at the anterior end 20 and the posterior end 22. FIG. 3B shows an endplate with a built-in lordotic angle 4. FIGS. 4A and 4B show the positioning of an implanted spinal fusion device 10.

The implanted spinal fusion device 10 may be filled with bone graft to facilitate the growth of bone through the fusion device. A bone substitute material, such as demineralized bone matrix, calcium phosphate, calcium sulfate or synthetic bone substitute materials, can also be packed within the fusion device. The bone graft is placed within the central cavity 82 of spacer 24 (see FIG. 5) before the spacer 24 is inserted between the endplates 12 and 14.

Figure 9A:
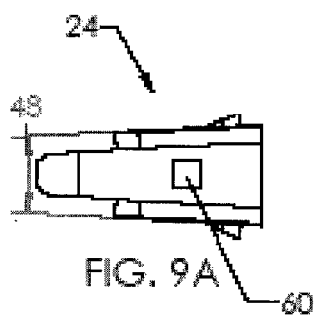
FIG. 9A is a side view of a tapered spacer which can form part of the of the spinal fusion device.
Figure 9B:
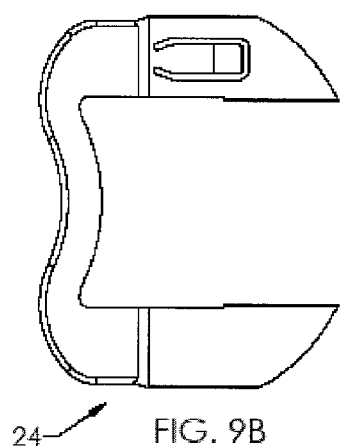
FIG. 9B is a top view of a spacer with cross bars at both the anterior and posterior ends.

In one embodiment, the spacer 24 has an open anterior end, as shown in FIG. 9B, that allows insertion of the bone graft after the spacer as been assembled with the engaging endplates. This embodiment of the spacer 24 may further contain an optional retaining plate that is attached to the anterior end of the spacer 24 after the insertion of the bone graft to prevent migration of bone graft after implantation.

Referring again to FIG. 1, the spacer 24 provides support to the engaging endplates and provides a predetermined spacing between the outer surfaces 16 and 17 of plates 12 and 14. The predetermined spacing is approximately equal to the height of the disc material that occupied the disc space between the vertebral bodies when the disc was healthy. As shown in FIG. 1, the spacer 24 may include two arms 44 and 46 that extend between the plates 12 and 14 along the length of the spinal fusion device 10 from the anterior end 20 to the posterior end 22.

Figure 5:
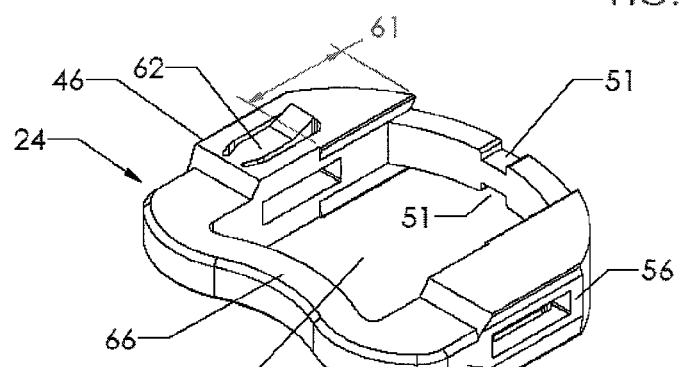
FIG. 5 is a perspective view of a spacer which forms part of the spinal fusion device of FIG. 1.
Figure 6:
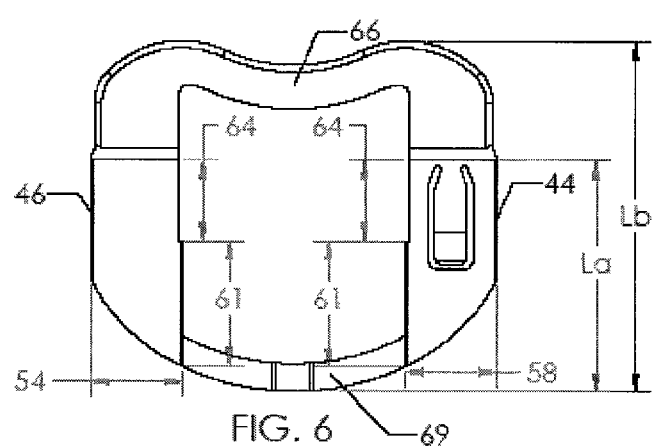
FIG. 6 is a top view of the spacer of FIG. 5.

As shown in FIGS. 5 and 6, the arms 44 and 46 may be substantially parallel to each other and are connected at both the posterior and anterior ends by connectors 66 and 69, respectively. The connectors 66 and 69 help share the load with the engaging endplates 12 and 14 and the arms 44 and 46 of the spacer 24. The connectors 66 and 69 also prevent migration of bone graft from the spinal fusion device in the posterior and anterior directions. As shown in FIG. 7A, the thickness of the connectors 66 and 69 may be defined as the spacer height ($h_s$). The connector 69 may further contain notches 51 to allow clearance for tabs on a spacer inserter 114 as it is being released after the implant has been assembled. Each arm may contain one or more flexible locking tab 62, a sidewall 56, and a side pocket 60. As shown in FIG. 7A, threaded hole 67 and slot 68 in the anterior side of spacer 24 allow for a positive attachment with the spacer inserter 114 shown in FIG. 27. Threaded hole 67 of spacer 24 attaches with the corresponding threaded rod 121 of spacer inserter 114. Slot 68 of spacer 24 may engage with a corresponding pin 123 of spacer inserter 114 to prevent rotation of the spacer after it has been attached to the spacer inserter.

With continued reference to FIGS. 6 and 7A, the arm 44 of the spacer 24 may include a pair of sliding ends 50 and the arm 46 of the spacer 24 includes a pair of sliding ends 52. The sliding ends 50 and 52 have end widths 54 and 58, respectively, that are greater than the width of the midsection of the arms 44 and 46, thus forming dovetail shaped sliding ends 50 and 52 that fit into the corresponding slots 70 on the endplates 12 and 14. Once assembled, the edges of the dovetail shaped sliding ends 50 and 52 engage with the side walls of the dovetail shaped slots 70 and hold the spacer and the corresponding endplate together. In an embodiment, the dovetail shaped sliding ends 50 and 52 and have a length that is the same as the length ($L_a$) of the arms 44 and 46. In certain embodiments, the length $L_a$ may be about 50%-80%, 55%-75%, 60%-70% or 66%-67% of the overall length ($L_b$) of the spacer 24.

As shown in FIG. 6, sliding ends 50 and 52 may contain only a partial dovetail (i.e., a dovetail section 61 that is shorter than the length (La) of the arms 44 and 46) to aid in assembly with the engaging endplates during insertion. Specifically, the partial dovetail design makes it easier for a surgeon to adjust the position of the spacer 24 between the endplates 12 and 14 and engage the spacer 24 with the endplates 12 and 14. With a portion of the dovetail removed, shown as 64 in FIG. 6, this portion of arms 44 and 46 enters the mating dovetail slots 70 in endplates 12 and 14 first while the spacer is being used to distract the endplates, which may not be parallel. This design thus allows the spacer 24 to extend in between the endplates 12 and 14 in a posterior direction and thus separate the endplates 12 and 14 in a parallel fashion, before the dovetails 61 of the spacer 24 engage with the mating dovetail slots 70 of endplates 12 and 14. In certain embodiments, the length 61 may be about 25%-50%, 30%-45%, 33%-40% or 36%-37% of the overall length ($L_b$) of the spacer 24.

FIG. 7B shows a cross-section of an embodiment of the flexible locking tab 62. The flexible locking tab 62 may include a cantilever structure 55 formed over a space 53. The cantilever structure 55 contains a protrusion 59 that locks into the locking slot 38 on endplates 12 and 14. The protrusion 59 contains a sloped front wall 64 that allows the cantilever structure 55 to be depressed into the space 53 when the spacer 24 is pushed into the space between the endplates 12 and 14 in the anterior-to-posterior direction. The cantilever 55 bounces back when the protrusion 59 reaches the locking slot 38 and self-locks into the locking slot 38. Such a design renders it possible to assemble the spinal fusion device 10 in situ by inserting the endplates 12 and 14 into a disc space and then inserting the spacer 24 between the two endplates and advancing the spacer 24 towards the posterior end of the endplates until the flexible locking tabs 62 on the spacer 24 lock into the corresponding lock slots 38 on the endplates.

In certain embodiments, the protrusion 59 may also contain a sloped back wall 65 that allows the protrusion 59 to be disengaged from the locking slot 38 by pulling the spacer 24 in the posterior-to-anterior direction with sufficient force. The sloped back wall 65 makes it possible to dissemble an implanted spinal fusion device in situ by pulling out the spacer 24 and then remove the endplates 12 and 14. Such a releasable design allows a surgeon to remove the spinal fusion device or to replace the endplate/spacer with an endplate/spacer of different size or height.

As shown in FIG. 7C, the front wall 64 of the protrusion 59 forms an angle 57 with the top surface of the spacer and the back wall 65 of the protrusion 59 forms an angle 63 with the top surface of the spacer. In certain embodiments, the angle 57 is in the range of about 120-170 degrees, preferably 135-160 degrees, and the angle 63 is in the range of 95-135 degrees, preferably 105-120 degrees. In another embodiment the angle 63 is about 90 degrees and does not allow the spacer 24 to be disengaged from the endplates when a force is applied to spacer 24 in the posterior-to-anterior direction.

The number and position of the flexible locking tab 62 may vary in various designs of the spinal fusion device 10. In certain embodiments, the flexible locking tab 62 are formed on the endplates and lock into corresponding slots formed on the spacer.

With reference now to FIGS. 8A and 8B, the slots 70 may be sized to accommodate the dovetail shaped sliding ends 50 and 52 of the spacer 24 and hold the spacer 24 in place. The spacer 24 can be coupled to the engaging endplates 12 and 14 by sliding the sliding ends 50 and 52 into the slots 70 in the anterior-to-posterior direction. The flexible tab 62 is pressed downward into space 53 (FIG. 7B) during the insertion process until the tab 62 reaches and locks into the slot 38 of the engaging endplate. The endplate 12 further contains a dovetail shaped slot 72 that engages with an endplate inserter during the assembling process. The inner surface 15 of endplate 14 is substantially similar to that of the endplate 12.

Figure 8C:
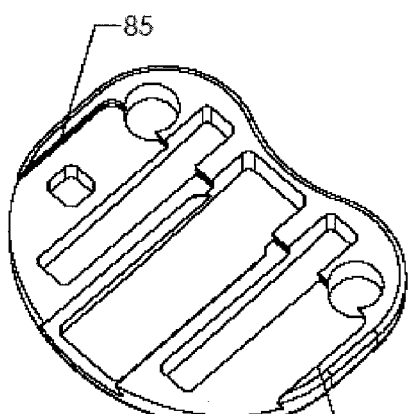
FIG. 8C is plan view of the inner surface of another embodiment of an endplate of the spinal fusion device of FIG. 1.
Figure 8D:
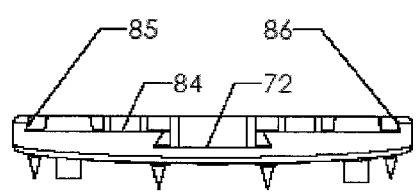
FIG. 8D is a front view of the endplate of FIG. 8C.
Figure 8E:
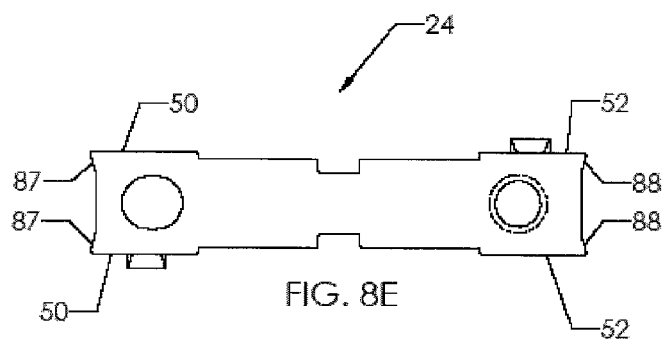
FIG. 8E is a front view of a spacer with sliding ends that match the center dovetail slot of the endplate of FIG. 8C.

FIGS. 8C and 8D show another embodiment of the end plates 12 and 14. In this embodiment, each endplate may contain one large centered dovetail slot 84 as opposed to two side dovetail slots 70 for engaging with the spacer 24. Specifically, the sidewalls 85 and 86 of the dovetail slot 84 interact with the edges 87 and 88 of the sliding ends 50 and 52, respectively, thus coupling the spacer 24 to the endplate. The inserter dovetail slot 72 is formed above the centered dovetail slot 84. FIG. 8E is a front view of a spacer 24 with sliding ends that match the centered dovetail slot 84 of the endplate.

The engaging endplates 12 and 14 may have substantially identical or different lordotic angles. In certain embodiments, the lordotic angle of the fusion device 10 is created by the endplates 12 and/or 14. The spacer 24 may has have the same predetermined height along the length of sliding ends 50 and 52. Spacers 24 of different heights ($h_s$) may be used to assemble with the engaging endplates 12 and 14 to allow the assembled construct height to be custom fit to various patient disc space heights.

In other embodiments, the lordotic angle of the fusion device is created by the spacer 24. FIG. 9A shows a taped single spacer 24 with variable height along the length of sliding ends 50 and 52. When this spacer 24 is positioned between the engaging endplates 12 and 14, the height of the assembled fusion device 10 decreases in a direction from the anterior end 20 to the posterior end 22 to maintain the natural lordotic angle of the human spine. The predetermined angle 48 of the spacer 24 corresponds to the desired lordotic angle of the patient at the affected level.

Figure 10:
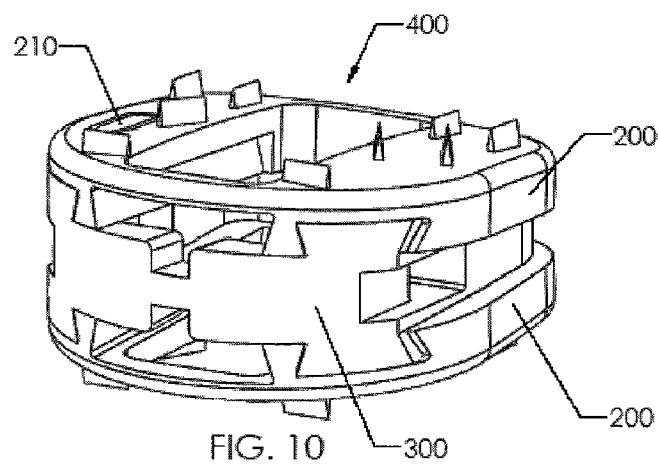
FIG. 10 is a perspective view of another embodiment of a spinal fusion device.
Figure 11:
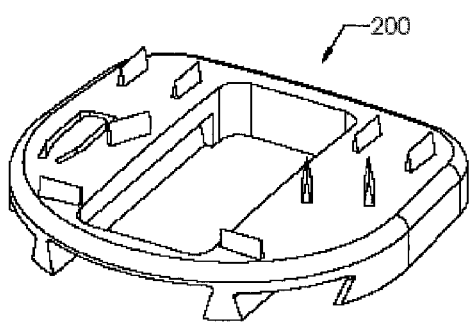
FIG. 11 is a perspective view of an endplate of the spinal fusion device of FIG. 10.
Figure 12:
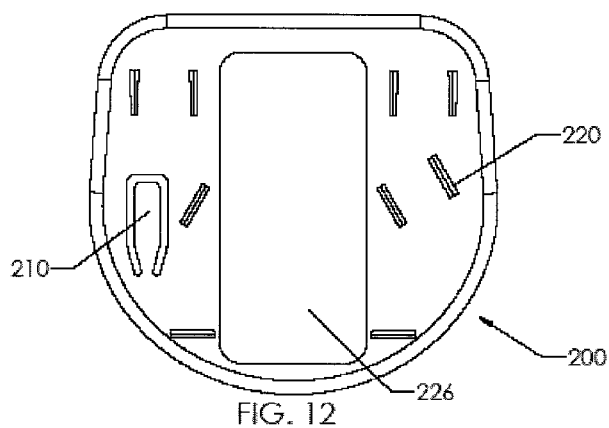
FIG. 12 is a top view of the endplate of FIG. 11.
Figure 13:
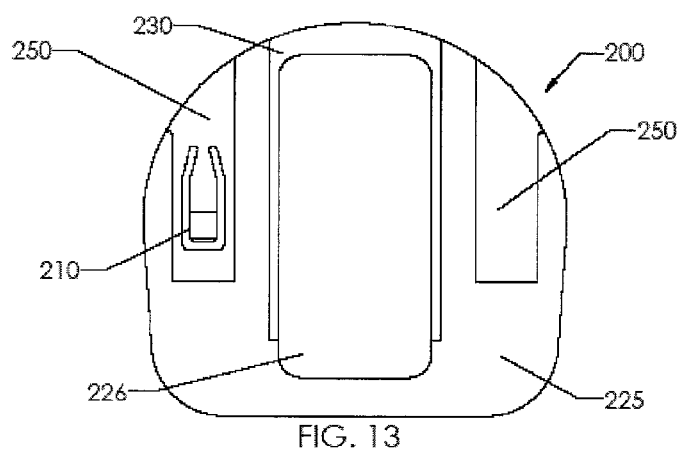
FIG. 13 is a bottom view of the endplate of FIG. 11.
Figure 14:
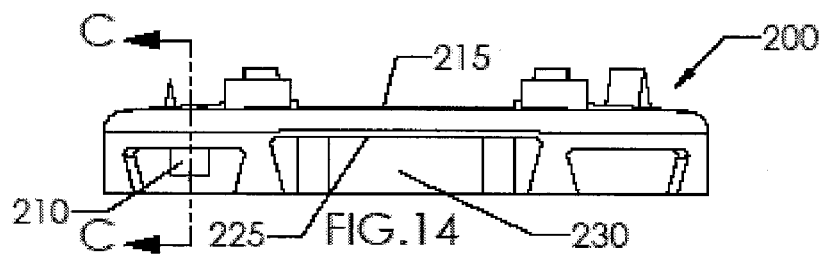
FIG. 14 is a front view of the endplate of FIG. 11.

Referring now to FIGS. 10-20, there is shown another embodiment of a spinal fusion device 400. As shown in FIG. 10, the spinal fusion device 400 generally includes two identical endplates 200 and a spacer 300 therebetween. The spinal fusion device 400 may be used in the cervical spine through an anterior approach, or sized to be used in the lumbar spine as well. In this embodiment, the endplates 200 are designed with a shape to fit the ends of adjacent cervical vertebrae.

Figure 15:
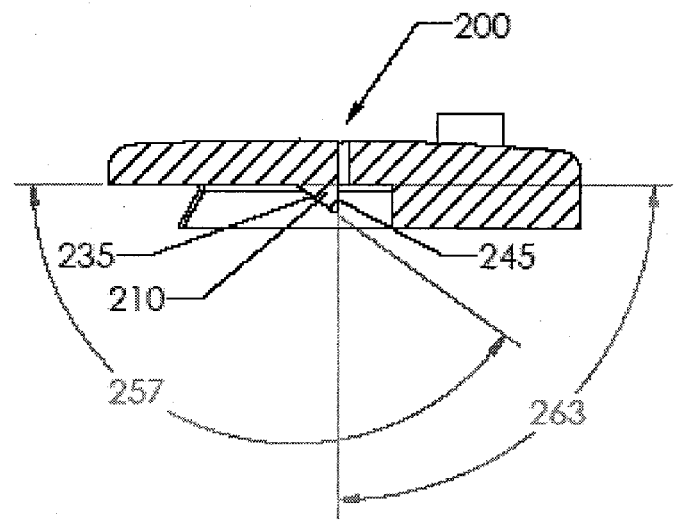
FIG. 15 is a cross sectional view of the endplate of FIG. 14 taken along line C-C.

Referring now to FIGS. 11-15, each endplate 200 may contain a flexible tab 210 for locking into a corresponding slot 320 on the spacer 300 and a series of projections 220 extending from the outer faces 215 of the respective endplate 200 for fixation of the engaging plates 200 with the cervical vertebral endplates. The endplate 200 may also contain a pair of side dovetail slots 250 on its inner surface 225 to receive the corresponding dovetail sliding plates on the spacer 300 and a center dovetail slot 230 to receive the corresponding structure on the endplate inserter. As shown in FIG. 15, the flexible tab 210 extends into the slot 250. The sloped front wall 235 of the flexible tab 210 allows the tab to be pushed upward while the spacer 300 is being assembled with the endplates 200 and to lock into the corresponding structures on the spacer 300 in a full assembled spinal fusion device. In this embodiment, the tab 210 has an end wall 245 that is substantially perpendicular to the inner surface 225 of the endplate 200. In other embodiments, the tab 210 has a sloped end wall 245. In certain embodiments, the front wall 235 forms an angle 257 of about 120-170 degrees, preferably 135-150 degrees with the inner surface 225. In other embodiments, the end wall 245 forms an angle 263 of 95-135 degrees, preferably 105-120 degrees with the inner surface 225.

Figure 16:
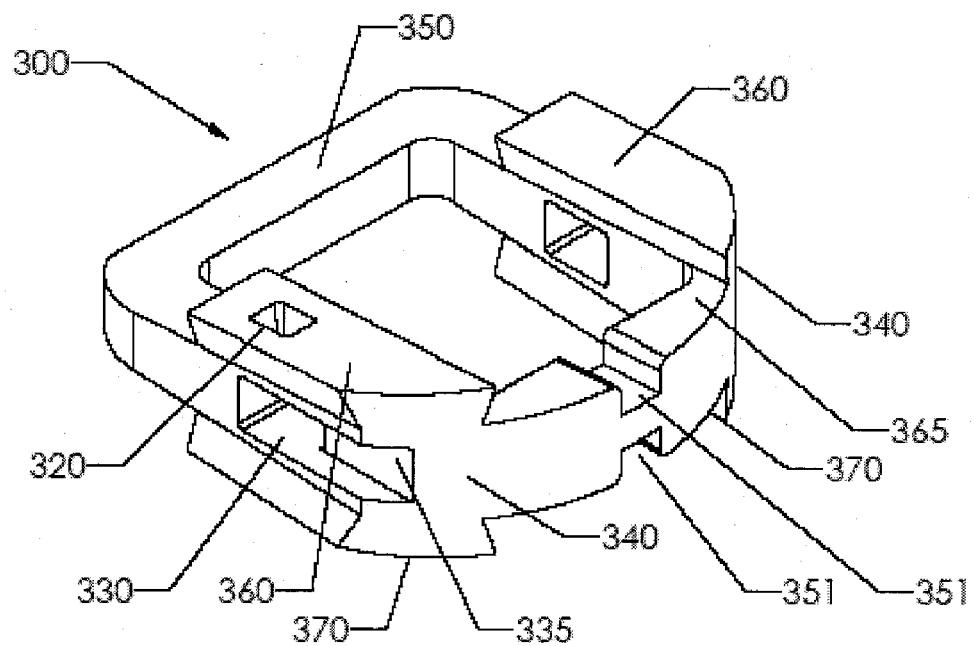
FIG. 16 is a perspective view of a spacer which forms part of the spinal fusion device of FIG. 10.
Figure 17:
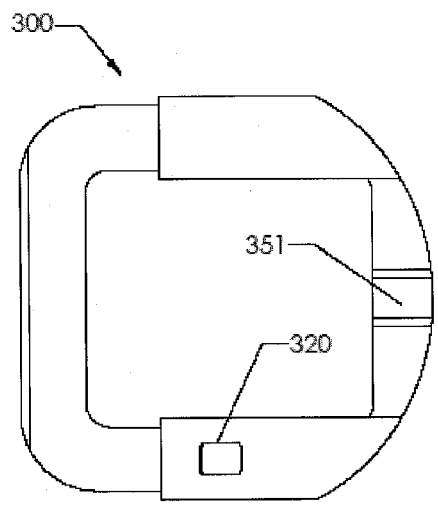
FIG. 17 is a top view of the spacer of FIG. 16.
Figure 18:
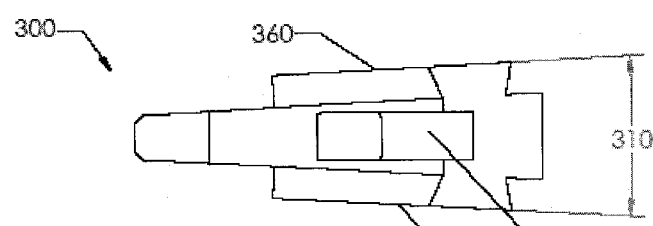
FIG. 18 is a side view of the spacer of FIG. 16.

Referring now to FIGS. 16-18, the spacer 300 may contain two arms 340, and connectors 350 and 365 that connect the arms 340 at the posterior and anterior ends respectively. As shown in FIG. 18, the outer surfaces 360 and 370 of the arms 340 form an angle 310 to maintain the natural lordotic angle in the cervical spine. Since the lordotic angle is created with the spacer 300, the engaging endplates 200 may be essentially flat. The spacer 300 contains a slot 320 on each arm 340 to captures the flexible tab 210 of the engaging endplates 200 during assembly to lock the spacer 300 to both the top and bottom engaging endplates 200. In this embodiment, one slot 320 is located on the outer surface 360 of one arm 340 and another slot 320 is located on the opposite outer surface 370 of another arm 340 so as to receive the flexible tab 210 from each endplate 200. The spacer 300 may further contain a side pocket 330 in each arm 340 to receive a corresponding structure on the spacer inserter. The connector 365 may further contain notches 351 to allow clearance for tabs on a spacer inserter as it is being released after the implant has been assembled.

Figure 19:
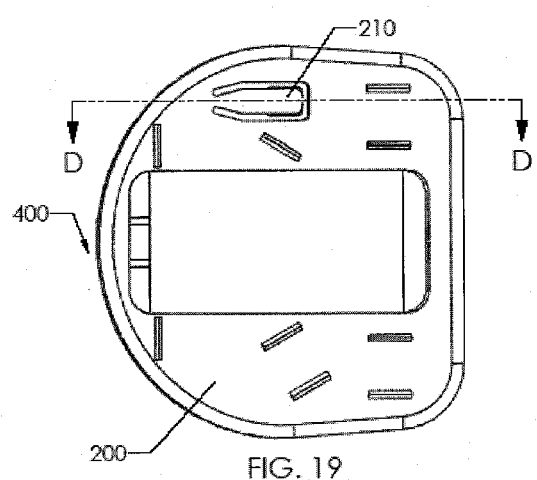
FIG. 19 is a top view of the spinal fusion device of FIG. 10.
Figure 20:
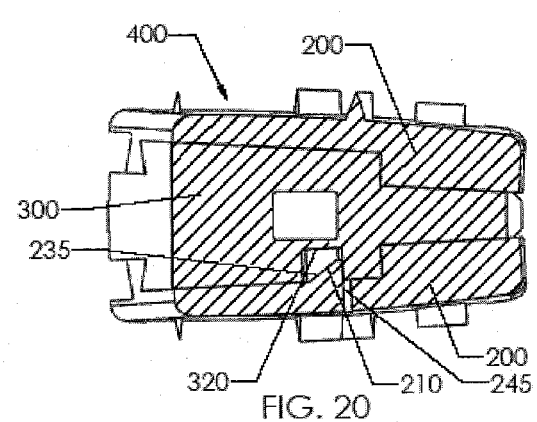
FIG. 20 is a cross sectional view of the spinal fusion device of FIG. 19, taken along line D-D.

An completely assembled spinal fusion device 400 is shown in FIGS. 19 and 20. The cross-sectional view of the device (FIG. 20) shows that the spacer 300 creates the desired lordotic angle. As noted earlier, while the tab 210 shown in FIG. 20 has an end wall 245 that is substantially perpendicular to the inner surface 225 of the endplate 200, the tab 210 may have a sloped end wall 245 so that an implanted fusion device 400 may be dissembled in situ by pulling the spacer 300 out of the engaged position with sufficient force that disengages the tab 210 from the pocket 320.

The endplates of the spinal fusion devices may be constructed with a biocompatible material with sufficient strength. Examples of such materials include, but are not limited to, metals such as titanium, stainless steel, cobalt-chromium-molybdenum, titanium alloy and other alloys, polymers such as polyetheretherketone (PEEK), ceramics, composites such as carbon fiber reinforced PEEK. In one embodiment, the endplates are constructed with a titanium alloy, such as a titanium-aluminum-vanadium alloy.

Similarly, the spacers of the spinal fusion devices may be constructed with a biocompatible material with sufficient strength. Examples of such materials include, but are not limited to, metals such as titanium, stainless steel, cobalt-chromium-molybdenum, titanium alloy and other alloys, polymers such as polyetheretherketone (PEEK), ceramics, composites such as carbon fiber reinforced PEEK. In one embodiment, the spacer is constructed with polyetheretherketone.

In some embodiments, surfaces of the engaging plates and/or spacer that contact bone may include a coating to promote osteointegration of the implant with bone. Examples of the coating include, but are not limited to, a titanium plasma spray, hydroxyapatite, or a bone morphogenetic protein.

In another embodiment, the spacer and/or endplates are made with a radiolucent material to allow the bone fusion mass to be seen on radiographic images.

Also disclosed are an instrumentation set and methods for implanting a spinal fusion device between adjacent vertebral bodies. The instrumentation set may include trial endplate and trial components, an endplate inserter, spacer inserters, hex drivers, and slap hammers. Trial components may be of various sizes and lordotic angles. An endplate inserter may be used to place the endplates between adjacent vertebral body after a discectomy has been performed. A spacer may be attached to a spacer inserter to guide the spacer through the endplate inserter.

Figure 31:
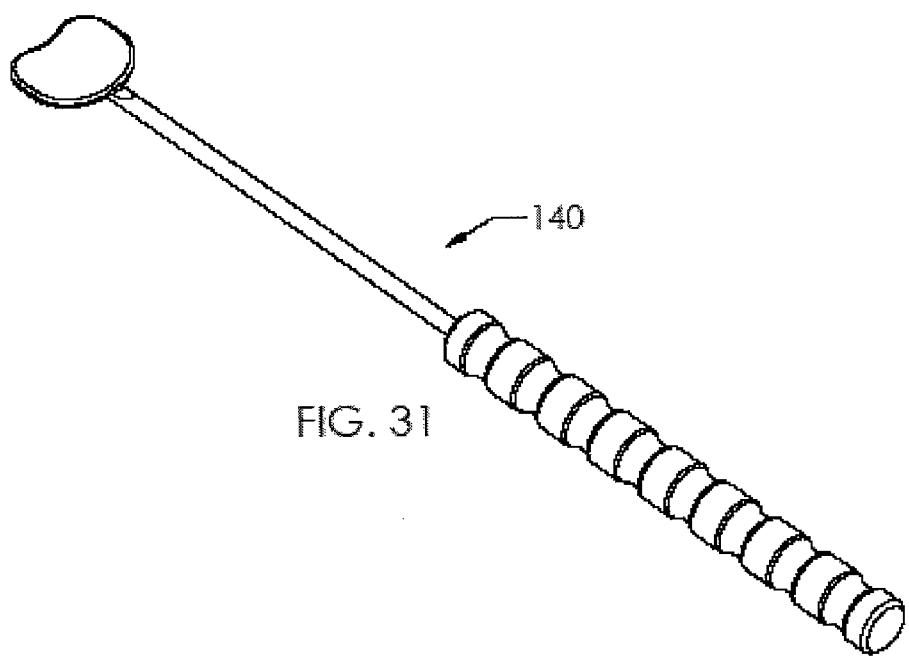
FIG. 31 is a perspective view of a thin endplate trial.
Figure 32:
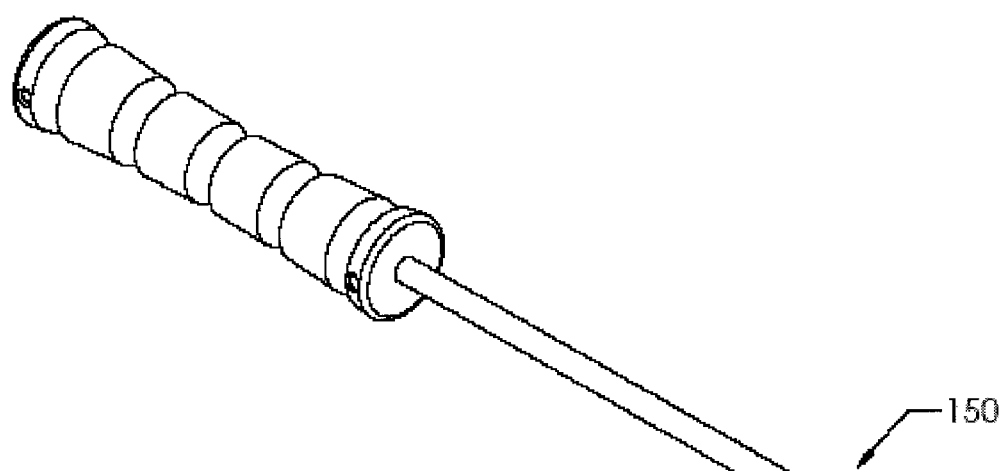
FIG. 32 is a perspective view of an implant construct trial.

With reference to FIG. 21, shown is an embodiment of a method 2100 for implanting embodiments of the spinal fusion device. To install embodiments of the spinal fusion device, a block discectomy may be performed with an anterior approach or a lateral approach. In an anterior approach, a surgical exposure of spine is created by passing through or going behind the abdominal cavity. In a lateral approach, the surgical exposure of spine is created by passing through the psoas muscle (transpsoas). The method 2100 may include preparing (block 2102) a spinal disc space between two adjacent vertebrae by removing the intervertebral disc along with anterior osteophytes adjacent to the interspace. The removing may be done using various techniques known in the art. The method 900 further includes determining (block 2104) the appropriate size endplate footprint using a thin endplate trial and determining (block 2106) the appropriately sized implant using an implant construct trial. As shown in FIG. 31, an endplate trial 140 is a thin plate that is used to determine the appropriate size of endplate in order to maximize endplate coverage of the ends of adjacent vertebrae and reduce the chance of subsidence. As is well known to a person of ordinary skill in the art, patients of different sizes and weight may require endplates of different sizes. A thin endplate trial 140 may be provided for each endplate footprint. FIG. 32 depicts an implant construct trial 150. A construct trial corresponds to the actual footprint, thickness, and lordotic angle between the vertebra formed by the assembly of the endplates with the spacer. The implant construct trial 150 allows a surgeon to select the appropriately sized implant to custom match the patient's own disc space. The surgeon is able to test every combination of implant that can be formed with engaging endplates and spacers.

An endplate inserter may be operationally coupled (block 2108) with a pair of endplates so that endplates may be inserted (block 2110) into the spinal disc space. A spacer may be coupled (block 2112) to a spacer inserter so that the spacer may be inserted (block 2114) into a lumen of the endplate inserter. When inserting the spacer, the spacer is advanced (block 2116) towards the posterior end of the endplates until the lock tabs on the spacer lock into the corresponding lock slots on the endplates. The spacer inserter is decoupled (2118) from the spacer inserter and the endplate inserter is decoupled (2120) from the endplates. The method may further include inserting bone graft or bone substitute into a central portion of the spinal fusion device.

Figure 22:
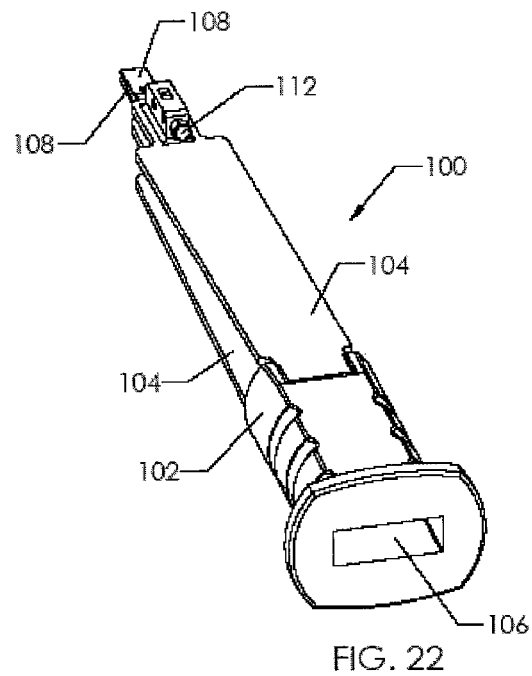
FIG. 22 is a perspective view of an embodiment of an endplate inserter.
Figure 23:
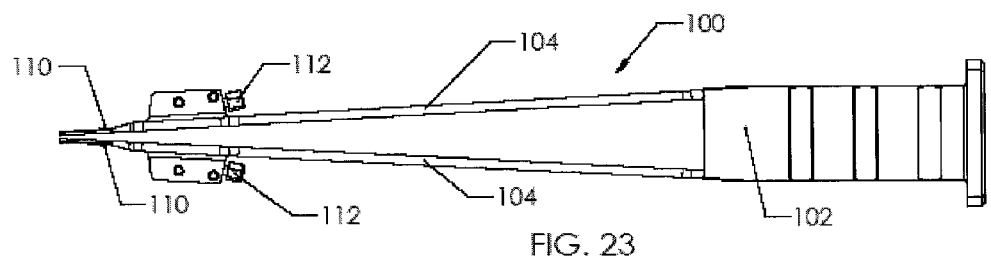
FIG. 23 is a side view of the endplate inserter of FIG. 22.
Figure 24:
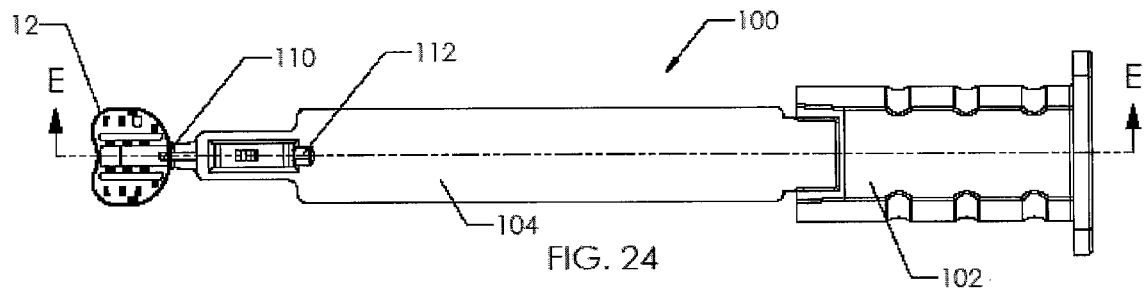
FIG. 24 is a top view of the endplate inserter of FIG. 22 coupled with the engaging endplates of the spinal fusion device.
Figure 25:
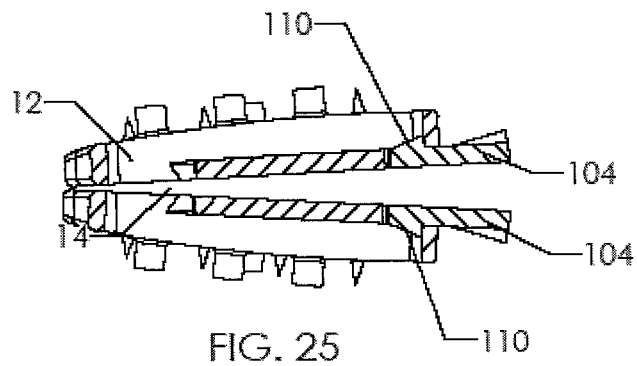
FIG. 25 is a partial section view, taken along line E-E of FIG. 24, of the engaging endplates coupled with the endplate inserter.

FIGS. 22 and 23 depict an embodiment of an endplate inserter 100. The endplate inserter 100 includes a handle 102 and flexible arms 104 that hold a pair of endplates. The handle 102 includes a lumen 106 that is sized to allow the insertion of a spacer between the endplates with a spacer inserter 114 (see FIG. 29A). Each arm 104 may include a coupling plate 108 that can be removably attached to an endplate. In one embodiment, the coupling plate 108 is a dovetailed plate that matches to a corresponding female dovetail slot 72 on the endplate (as shown in FIGS. 8A and 8B). The coupling plate 108 may further include tabs 110 that engage with the slot 26 of the endplate 12 or 14 to lock the inserter 100 to the endplate 12 or 14. FIG. 24 depicts an endplate inserter 100 with endplate 12 attached to the flexible arms 104.

Figure 26:
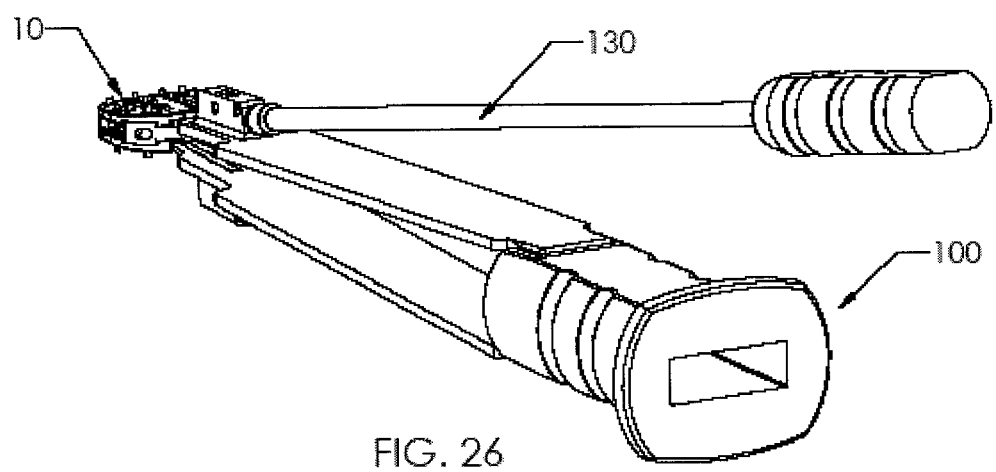
FIG. 26 is perspective view of the endplate inserter, the spinal fusion device, and a driver coupled together.

The arms 104 of the endplate inserter 100 are flexible to allow them to bend so spacers 24 of varying pre-determined heights can be passed through the inserter 100 and inserted between the engaging endplates 12 and 14. The inserter 100 may include a threaded screw 112 to allow tabs 110 to be opened or closed. When the screw 112 is advanced, the tab 110 is in the locked position that engages with the slot 26 of the endplates, thus securing the endplates 12 and 14 to the endplate inserter 100. When the screw 112 is backed out, the tab 110 is disengaged from the slot 26 to allow the inserter 100 to be separated from the endplates 12 and 14. The notch 51 in the spacer 24 allows an opening for the tab 110 to pass through the spacer 24 after the tab 110 is disengaged from the endplates 12 and 14 (See FIGS. 5 and 7A). As shown in FIG. 26, a driver 130 may be used to turn the screw 112 to disengage the tab 110 of the endplate inserter 100 from the slot 26 of the engaging endplates.

Figure 27:
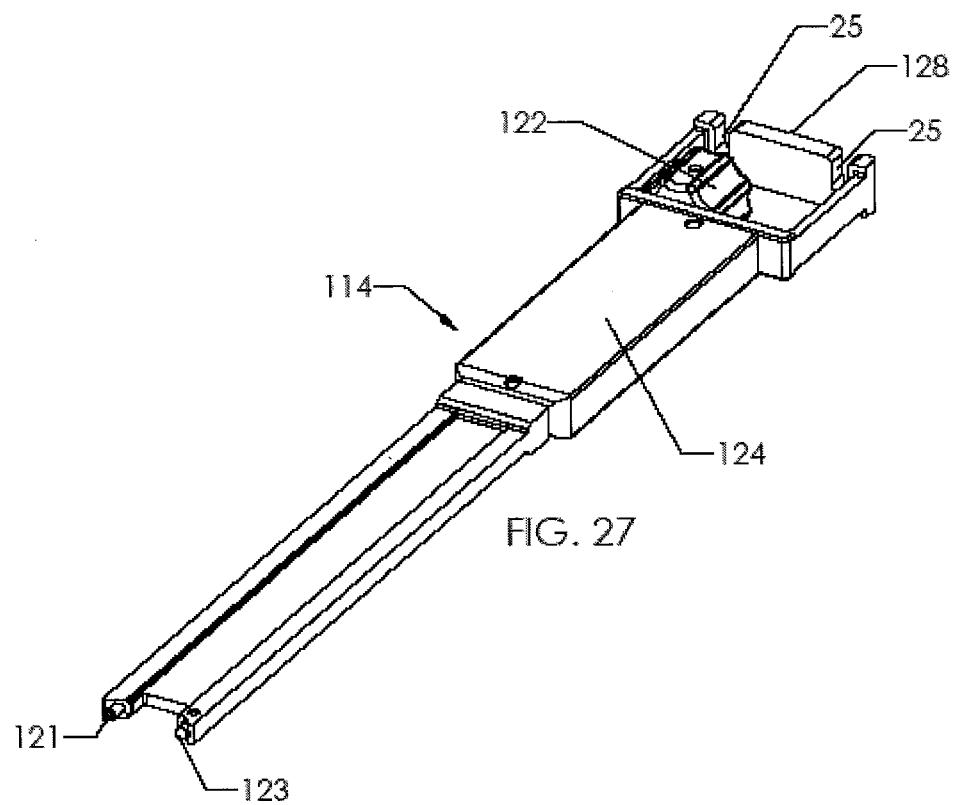
FIG. 27 is a perspective view of an embodiment of a spacer inserter.
Figure 28:
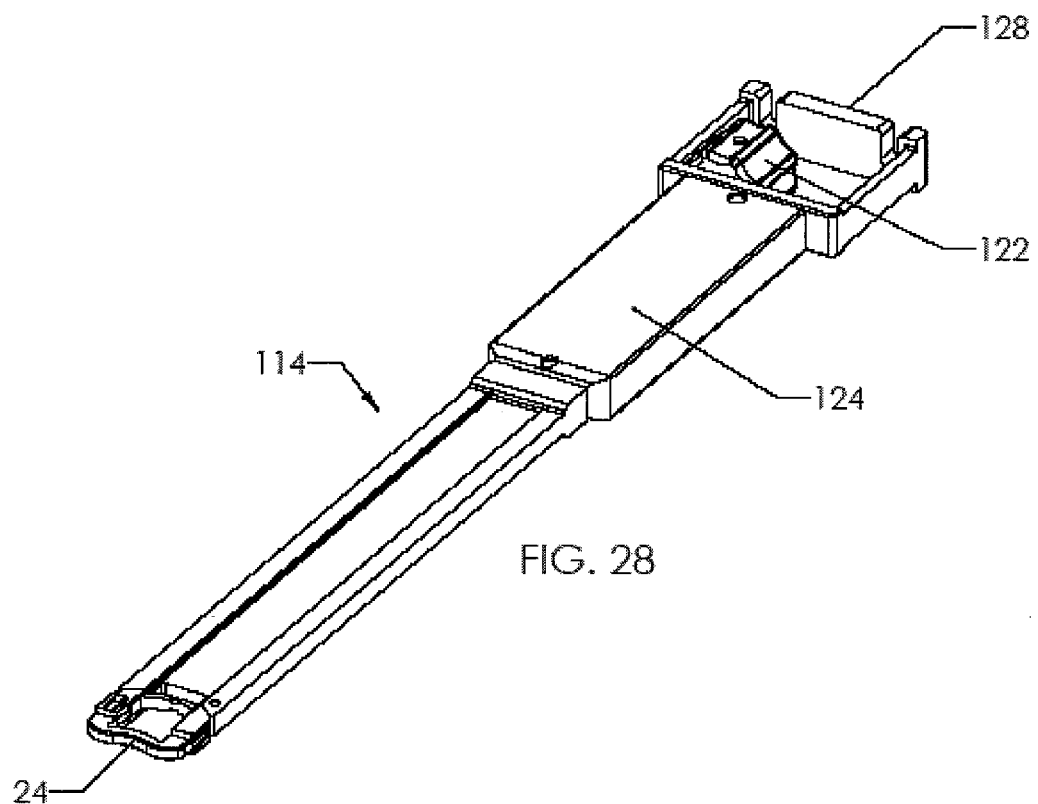
FIG. 28 is a perspective view of the spacer inserter of FIG. 27 coupled with a spacer according to the present invention.

FIG. 27 depicts a perspective view of a spacer inserter 114. The spacer inserter 114 includes a rotating threaded shaft 121 and a fixed pin 123, a inserter body 124, and a turning knob 122. The threaded shaft 121 may be rotated by turning knob 122 and thus engaging the threaded shaft with the threaded hole 67 in spacer 24. The fixed pin 123 of spacer inserter 114 engages with the mating slot 68 of spacer 24 to prevent the spacer from rotating once it has been coupled with the spacer inserter 114. FIG. 28 shows a perspective view of the spacer 24 coupled with the spacer inserter 114.

Figure 29A:
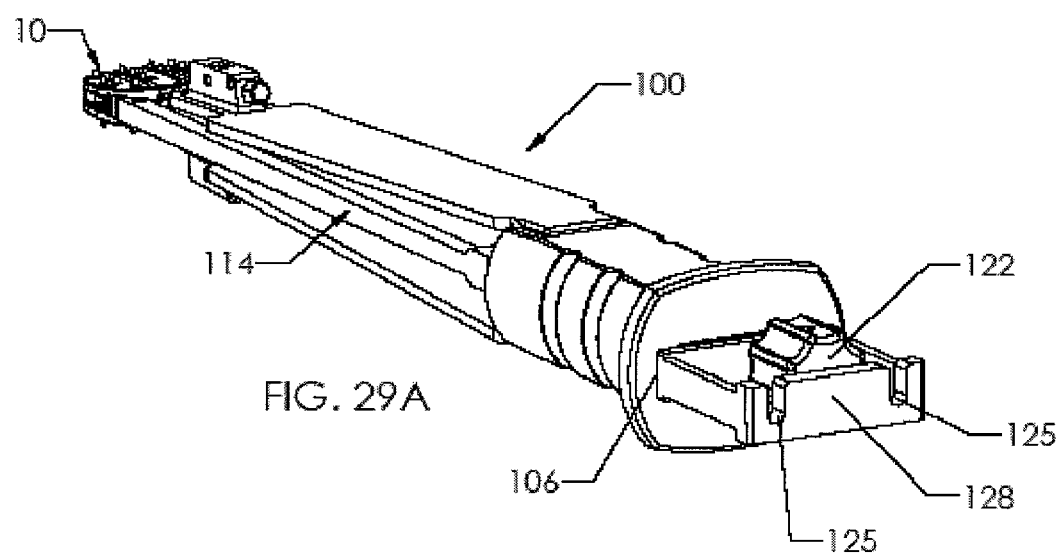
FIG. 29A is a perspective view of the endplate inserter, the spacer inserter, and the assembled spinal fusion device coupled together.
Figure 29B:
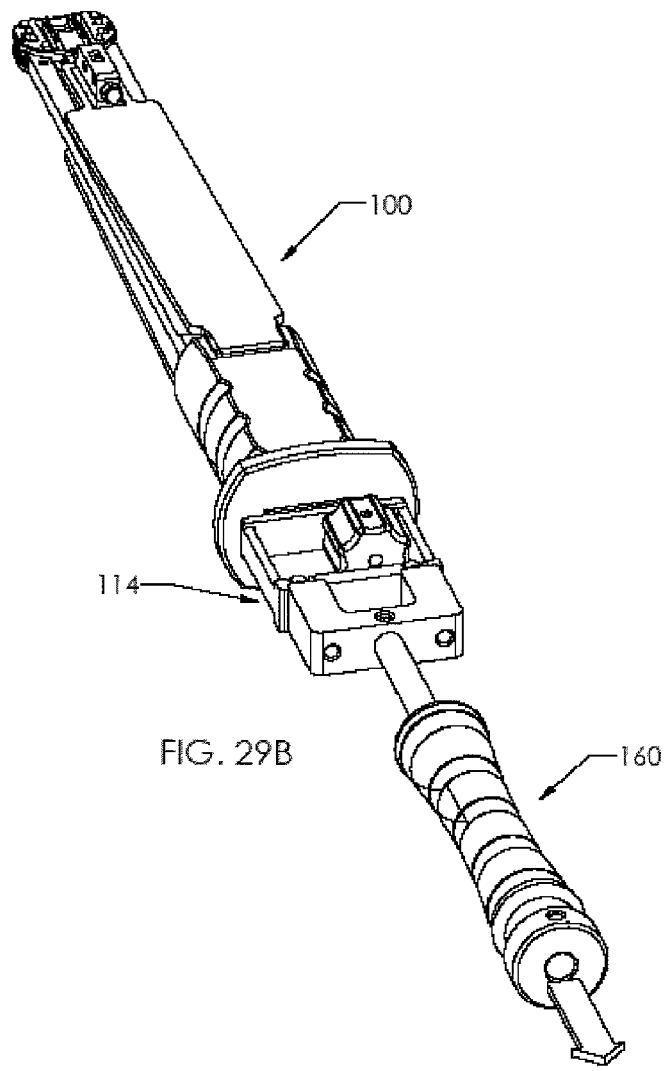
FIG. 29B is a perspective view of the endplate inserter, the spacer inserter, the assembled spinal fusion device, and the splaphammer coupled together.
Figure 30:
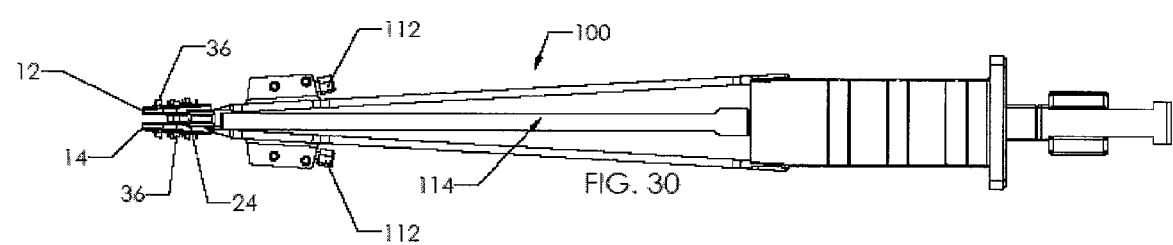
FIG. 30 is a side view of the endplate inserter, the spacer inserter, and the spacer being inserted between the engaging endplates.

Referring now to FIGS. 29A, 29B and 30, the body 124 of the spacer inserter 114 interfaces with the lumen 106 of endplate inserter 100 as depicted in the perspective view of FIG. 29. The clearance between the body 124 and the lumen 106 is minimized to provide a controlled delivery of the spacer 24 through the endplate inserter 100 and into the engaging endplates 12 and 14. Surface 128 of the spacer inserter 114 is an impact surface for interface with a mallet during the insertion of the spacer 24 between the endplates 12 and 14. Slots 125 of spacer inserter 114 are used to couple the inserter with a slap-hammer 160 to allow an impulse force to be applied to the spacer 24 to disengage the flexible tab 62 from the engaging slot 38 of the endplates 12 and 14, thus allowing the spacer to be removed from the endplates after assembly within the disc space. FIG. 29B shows the slap-hammer 160 attached to the spacer inserter 114.

FIG. 30 depicts a view of the spacer 24 entering the space between the endplates 12 and 14. In FIG. 30, the spacer 24 is not yet locked into the endplates 12 and 14, but has been sufficiently advanced into the space between the endplates 12 and 14 to separate the endplates into a substantially parallel position to allow engagement of the dovetails 61 of the sliding ends 50 and 52 with the corresponding slots 70 (not shown in FIG. 30) on the endplates 12 and 14. Separation of the endplates 12 and 14 by the spacer 24 may force projections 36 on the outer surfaces of the engaging plates into the bony end of the adjacent vertebrae to attach the endplates 12 and 14 to the body of the vertebrae (FIG. 4B).

While the instrumentation in FIGS. 22-32 is shown only with spinal fusion device 10, it is understood that the instrumentation set and the surgical procedure described above and shown in FIGS. 22-32 can also be used to insert the spinal fusion device 400 within the cervical or lumbar spine.

Figure 33:
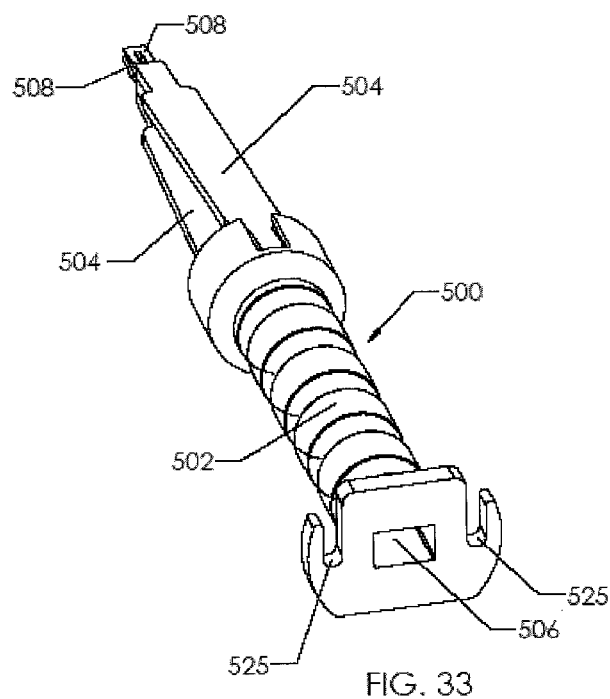
FIG. 33 is a perspective view of an endplate inserter used to insert endplates shown in FIGS. 11 and 12.
Figure 34:
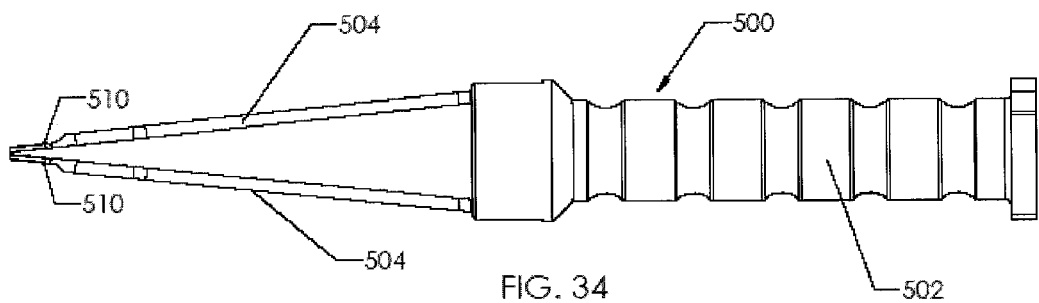
FIG. 34 is a side view of the endplate inserter of FIG. 33.
Figure 35:
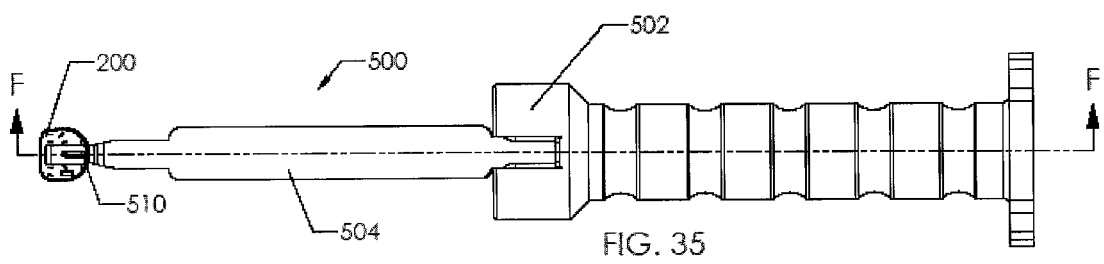
FIG. 35 is a top view of the endplate inserter of FIG. 32 coupled with the engaging endplates of the spinal fusion device of FIG. 10.
Figure 36:
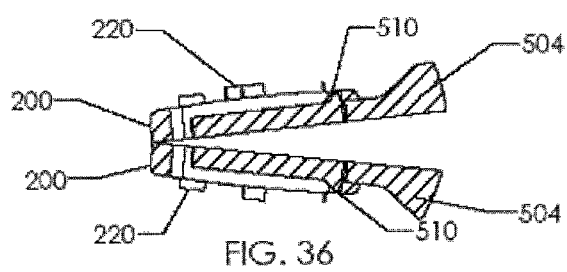
FIG. 36 is a partial section view, taken along line F-F of FIG. 35, of the engaging endplates coupled with the endplate inserter.

FIGS. 33 and 34 show another embodiment of an endplate inserter 500. Similar to the endplate inserter 100, the endplate inserter 500 may include a handle 502 and flexible arms 504 that hold a pair of endplates 200. The handle 502 includes a lumen 506 that is sized to allow the insertion of a spacer between the endplates with a spacer inserter 514. Each arm 504 includes a coupling plate 508 that can be removably attached to an endplate 200. In one embodiment, the coupling plate 508 is a dovetailed plate that matches to a corresponding female dovetail slot 230 on the endplate 200 (shown in FIG. 14). The coupling plate 508 may further include flexible tabs 510 that engages with the slot 226 of the endplate 200 to lock the inserter 500 to the endplate 200. The flexible tabs 510 are pressed downward during the insertion process until the tabs 510 reaches and lock up into the slot 226 of the engaging endplates 200. Slots 525 allow the attachment of a slap-hammer to the endplate inserter 500 to remove the endplate inserter 500 from an assembled spinal fusion device 400. FIG. 35 shows the endplate inserter 500 coupled the endplates 200. FIG. 36 is a partial cross sectional view along the line F-F of FIG. 5 showing the coupling mechanism between the endplates 200 and the endplate inserter 500.

Figures 37, 38:
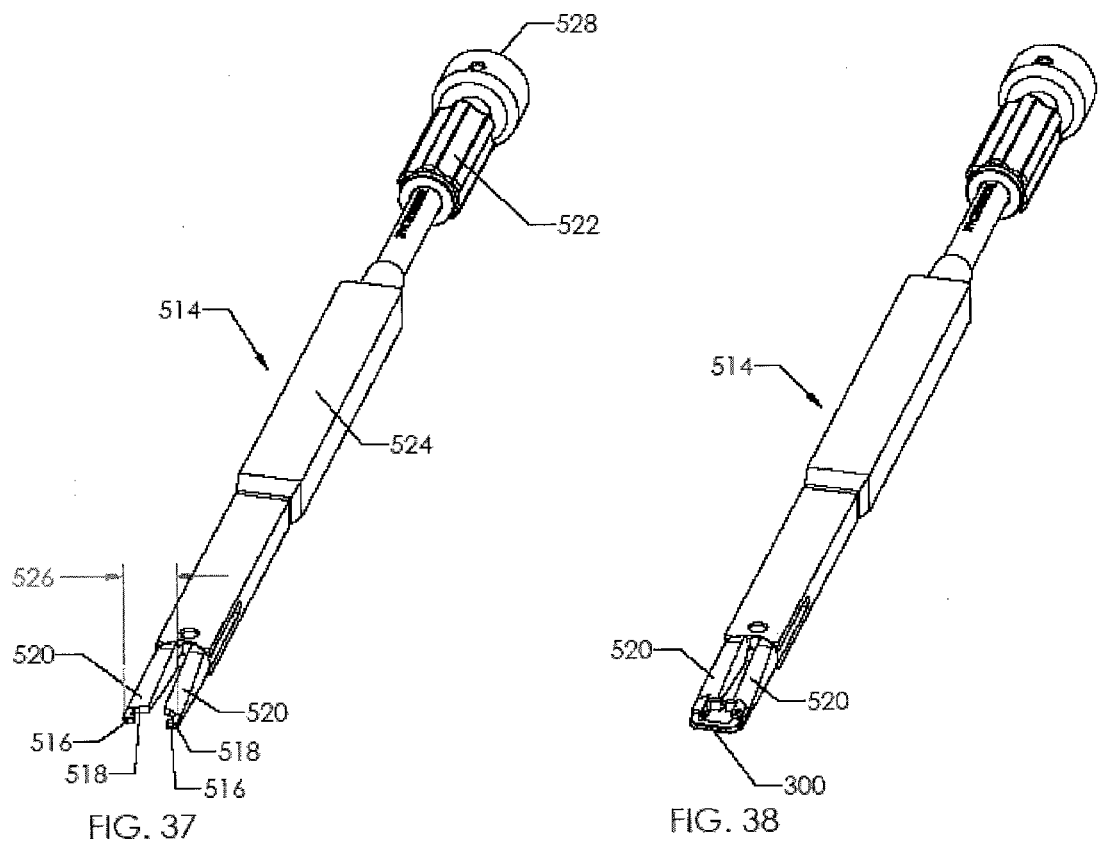
FIG. 37 is a perspective view of an embodiment of a spacer inserter.
FIG. 38 is a perspective view of the spacer inserter of FIG. 37 coupled with the spacer of FIG. 16.

FIG. 37 depicts a perspective view of another embodiment of spacer inserter 514. The spacer inserter 514 may include a pair of arms 520 to hold the spacer 300, an inserter body 524, and a turning knob 522. The arms 520 may include tabs 516 that couple with slots 330 of a spacer 300 (see FIG. 16). The tabs 516 allow the spacer 300 to be coupled with a spacer inserter 514. FIG. 38 shows a perspective view of the spacer 300 coupled with the spacer inserter 514. The arms 520 of the spacer inserter 514 may be spread wider by turning knob 522, thus increasing the distance 526 between tabs 516. Turning knob 522 in the opposite direction will shorten the distance 526 between the tabs 516 to provide a clamping force to the sides 335 of the spacer 300.

Figure 39:
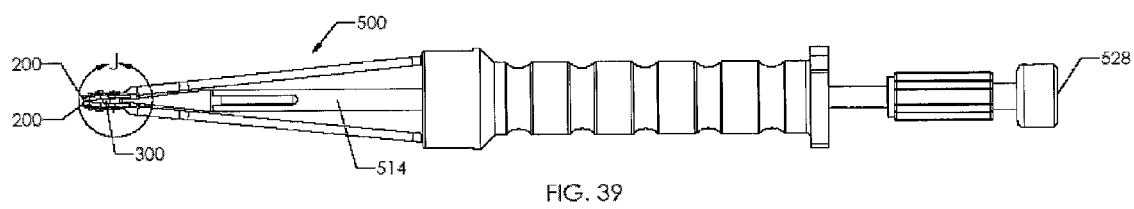
FIG. 39 is a side view of the endplate inserter, the spacer inserter and the spacer being inserted between the engaging endplates.
Figure 40:
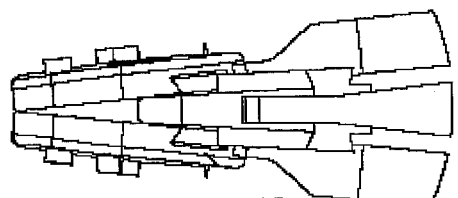
FIG. 40 is a view of detail circle J in FIG. 39.
Figure 41:
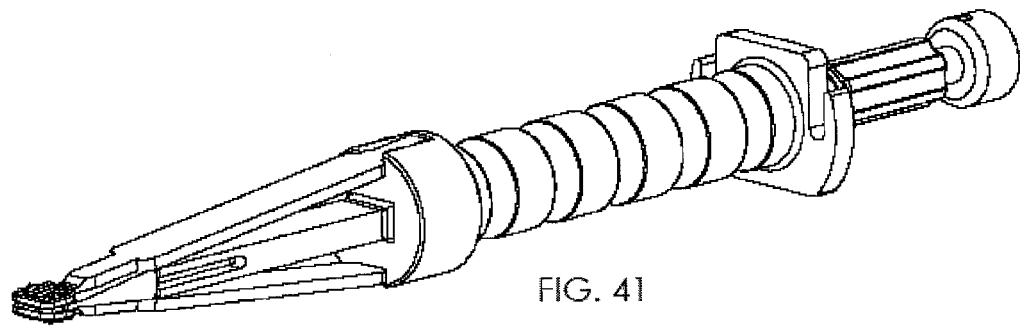
FIG. 41 is a perspective view of the endplate inserter, the spacer inserter and the assembled implant coupled together.

Referring to FIGS. 39 and 40, the body 524 of the spacer inserter 514 interfaces with the lumen of the endplate inserter 500. Surface 528 of the spacer inserter 514 is an impact surface for the interface with a mallet during the insertion of the spacer 300 between the endplates 200. The impact is passed to the spacer 300 through the surfaces 518 of the arms 120 to advance the spacer 300 between the engaging endplates 200. FIG. 41 shows the spacer 300 completely engaged and locked with the endplates 200 after the fusion device has been assembled in situ.

Figure 42:
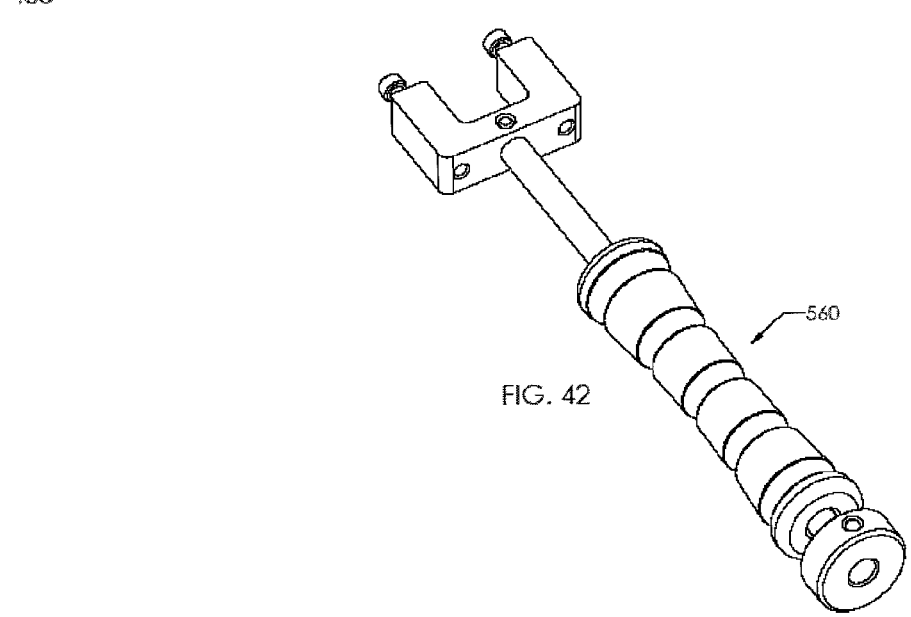
FIG. 42 is a perspective view of a slap-hammer.
Figure 43:
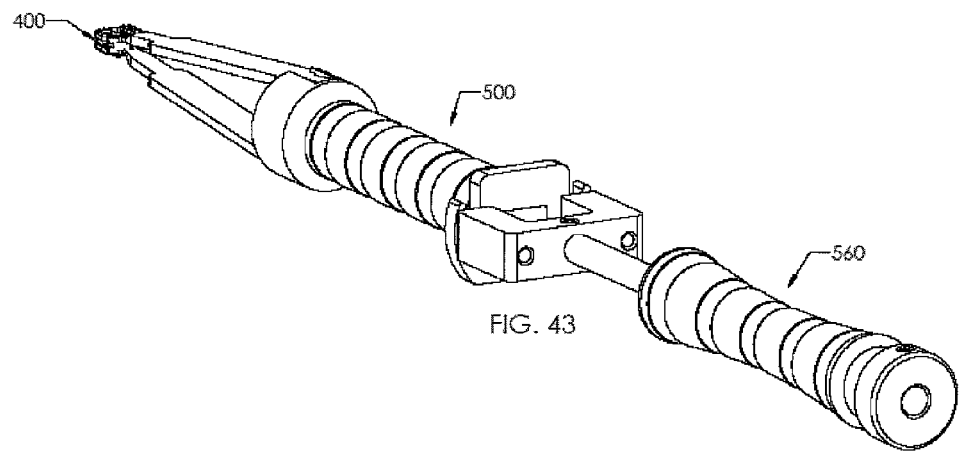
FIG. 43 is a perspective view of the assembled implant, the endplate inserter, and the slap-hammer coupled together.

Referring now to FIGS. 42 and 43, the endplate inserter 500 may be removed from the endplates 200 after the interbody construct 400 has been assembled by attaching a slaphammer 560 to the endplate inserter 500 and applying an impulse force to disengage the tabs 510 from the slots 226 in the endplates 200. A slot 351 in the spacer 300 allows an opening for the tab 510 to pass through the spacer 300 after the tab 510 is disengaged from the endplates 200 (See FIGS. 16 and 17).

Figures 44A, 44B:
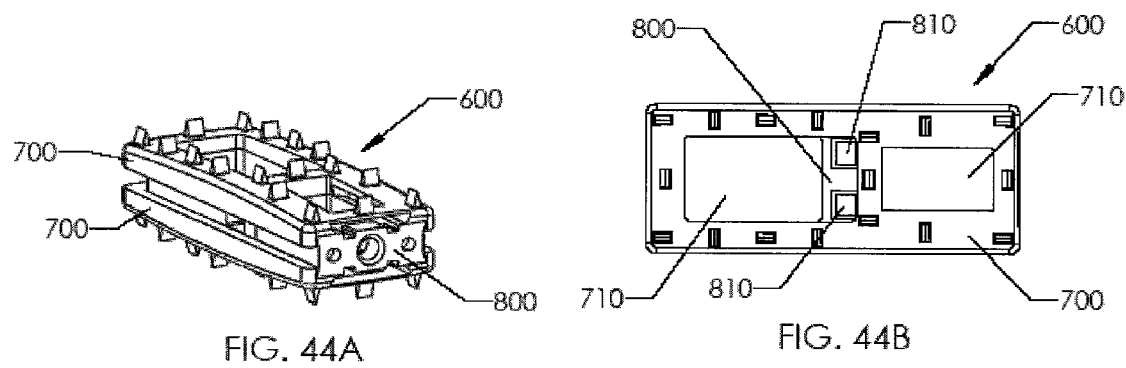
FIG. 44A is a perspective view of another embodiment of a spinal fusion device.
FIG. 44B is a top view of the spinal fusion device of FIG. 44A.
Figure 45:
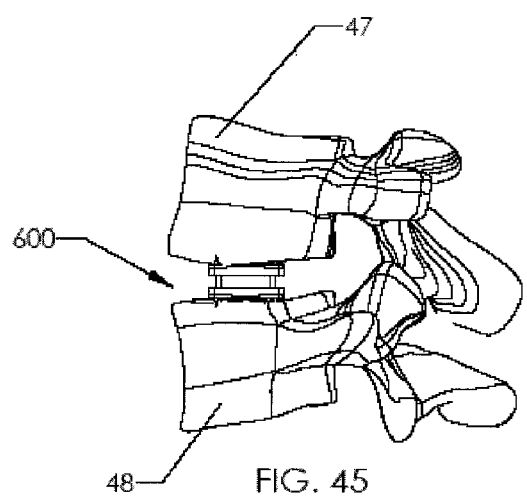
FIG. 45 is a side view of adjacent vertebral bodies with the spinal fusion device of FIG. 44A disposed therebetween.

Referring now to FIGS. 44A-50B, shown are various diagrams and views illustrating another embodiment of a spinal fusion device 600. As shown in FIG. 44A, the spinal fusion device 600 generally includes two endplates 700 and the spacer 800 therebetween. The spinal fusion device 600 can be used in the lumbar spine through a lateral approach. In this embodiment, the endplates 700 are designed with an outer surface 760 to be convex in shape to generally fit the concavity of the adjacent vertebral boney surface. FIG. 44B shows a top view of the endplate 700. FIG. 45 shows adjacent vertebral bodies with the spinal fusion device 600 disposed therebetween.

FIG. 46 shows the inner surface of the endplate 700. Each endplate 700 may contain two openings 710 for a bone graft to grow through the endplate 700 and allow fusion with an adjacent vertebrae, an edge 725 which provides a surface to engage with flexible tabs 810 of spacer 800, two central dovetail slots 720 and 730 to couple with the endplate inserter 900 and the spacer 800. The dovetail slots 720 and 730 may be centered on the bottom surface 740 of the endplate at two different depths so the spacer 800 can couple with the mating dovetail slot 720 in endplate 700 while simultaneously allowing an endplate inserter to be engaged with the dovetail slot 730 in the endplate. As shown in FIG. 47, which shows a side view of the end plate 700, the endplate 700 contains a series of projections 750 extending from the outer faces 760 of the endplates 700 for fixation of the engaging plates 700 with the lumbar vertebral bodies. The flexible tab 810 extends into the larger opening 710 while the surface 735 prevents the spacer 800 from accidental disengagement from the endplates 700 after assembly. The sloped wall 820 of the flexible tabs 810 allows the tabs 810 to be pushed away from the engaging endplate 700 while the spacer 800 is being assembled with the endplates. Once the flexible tab 810 enters the larger opening 710 in endplate 700, the flexible tab 810 snaps into the opening to lock the endplates 700 with the spacer 800 therebetween, as shown in FIGS. 44A and 44B.

FIGS. 49-50B show various views of the spacer 800, as shown in FIG. 49, the spacer 800 may contain sliding ends 840 and 850. The width 860 of sliding surfaces 840 and 850 are greater than the width of the midsection of the spacer 800, thus forming dovetail shaped sliding ends 840 and 850 that fit into the corresponding slots 720 of the endplates 700. The lead-in width 865 of the spacer 800 may be less than the dovetail width 860 to allow the spacer to slide in between the endplates 700 during initial assembly and separate the endplates 700 in a parallel fashion before the sliding ends 840 and 850 of spacer 800 engage with the corresponding dovetail slots 720 of endplates 700. In certain embodiments, the dovetail surfaces 840 and 850 have a length $L_c$ that may be about 20%-60%, 25%-50%, 30%-45% or 32%-40% of the overall length ($L_d$) of the spacer 800. FIG. 50A shows a front view of the spacer 800.

Referring again to FIGS. 49 and 50A, slots 870 at the anterior end of the spacer 800 allow clearance for locking tabs of endplate inserter 900 to pass through when disengaging the inserter 900 from the spinal fusion implant 600 after it has been assembled. As shown in FIG. 50B, the sloped wall 820 of the protrusion 810 forms an angle 857 with the top surface of the spacer and the back wall 830 of the protrusion 810 forms an angle 863 with the top surface of the spacer. In certain embodiments, the angle 857 is in the range of about 120-170 degrees, preferably 135-160 degrees, and the angle 863 is in the range of 95-135 degrees, preferably 105-120 degrees. In another embodiment the angle 863 is 90 degrees and does not allow the spacer to be disengaged from the endplates when a force is applied to spacer 800 in the direction opposite in which it was inserter into the endplates 700.

Figure 52:
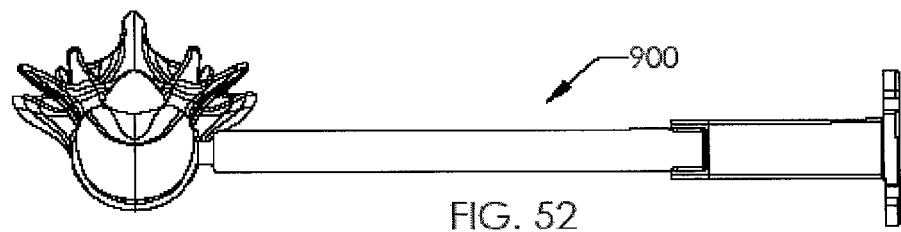
FIG. 52 is a top view of the endplate inserter coupled with the endplates being inserted in between the adjacent vertebrae using a lateral approach.
Figure 53:
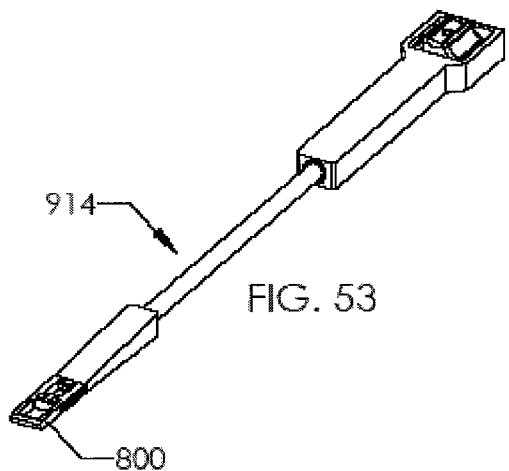
FIG. 53 is a perspective view of the spacer of FIG. 49 attached with an embodiment of a spacer inserter.
Figure 54:
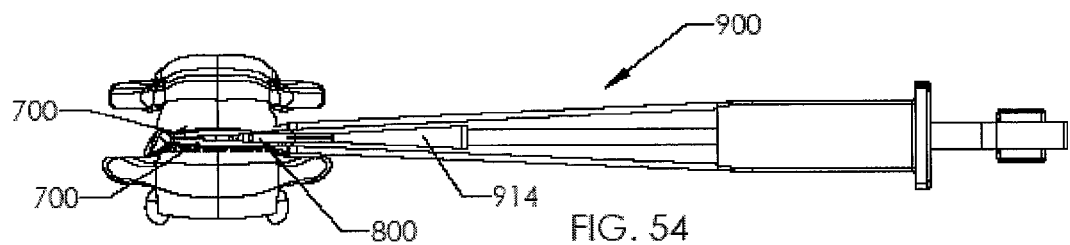
FIG. 54 is a side view of the endplate inserter, spacer inserter of FIG. 53 coupled with the spacer of FIG. 49 showing the spacer being inserted between the engaging endplates.
Figure 55:
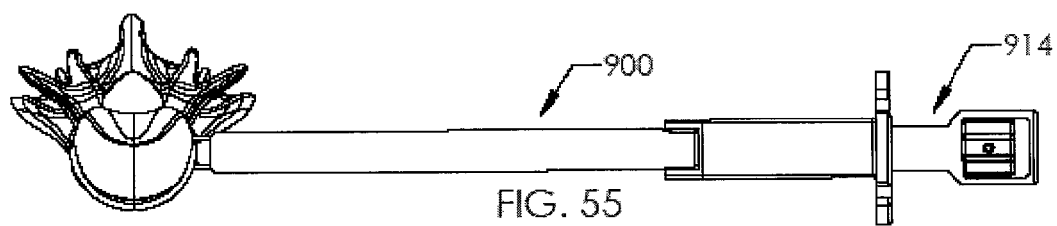
FIG. 55 is a top view of the endplate inserter, spacer inserter of FIG. 53 coupled with the spacer of FIG. 49 showing the spacer being inserted between the engaging endplates.
Figure 56:
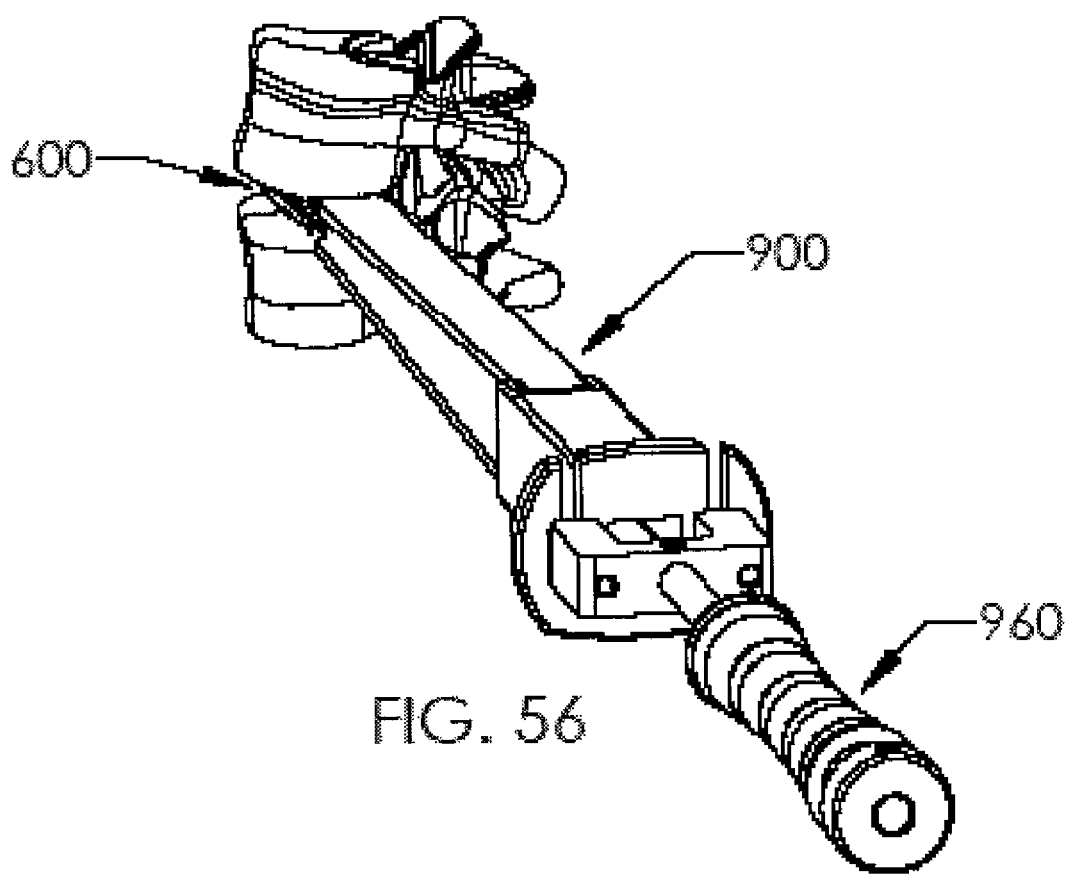
FIG. 56 is a perspective view of the assembled fusion implant of FIG. 44, the endplate inserter, and a slap-hammer coupled together.

FIGS. 51-56 show the approach and instrumentation used to assemble endplates 700 and spacer 800 to form spinal fusion implant 600. FIGS. 51 and 52 generally show the lateral approach used to insert the endplates 700 into a disc space using the endplate inserter 900. FIG. 53 shows the spacer 800 locked with the spacer inserter 914. FIGS. 54 and 55 show the spacer inserter 914 entering the lumen in the handle of endplate inserter 900 thus guiding the spacer 800 into the proper position between the two endplates 700. FIG. 56 shows the slap-hammer 960 coupled with the endplate inserter 900, to allow an impulse force to be applied to the endplate inserter 900 to decouple the inserter from the endplates 700 of the assembled spinal fusion implant 600. Force is applied in a direction away from the spine.

Also disclosed are spinal fusion kits that contain key components of the spinal fusion device. In one embodiment, a spinal fusion kit contains modular endplates with different sizes and lordotic angles and modular spacers with different sizes and lordotic angles. In another embodiment, the kit further contains a endplate inserter and a spacer inserter. In yet another embodiment, the kit further contains endplate trials of various footprint and construct trials of various footprint, thickness, and lordotic angles.

It is also understood that while the present invention has been described with respect to at least one embodiment, the invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims. Further modifications and alternative embodiments of various aspects of the invention will be apparent to those skilled in the art in view of this description. Accordingly, this description is to be construed as illustrative only and is for the purpose of teaching those skilled in the art of the general manner of carrying out the invention. Elements and materials may be substituted for those illustrated and described herein, parts and processes may be reversed, and certain features of the invention may be utilized independently, all as would be apparent to one skilled in the art of having the benefit of this description of the invention. Changes may be made to the elements described herein without departing from the spirit and scope of the invention as described in the following claims.

What is claimed is:

1. A spinal fusion device, comprising:
a first endplate configured for fitting within a disc space and engaging with a first vertebra, said first endplate has an anterior end and a posterior end; and
a second endplate configured for fitting within said disc space and engaging with a second vertebra, said second endplate has an anterior end and a posterior end,
wherein said endplates are separated by a single spacer that maintains a pre-determined distance between said endplates, said spacer comprising:
an anterior end;
a posterior end;
a first lateral side;
a second lateral side, opposite to said first lateral side;
a first surface that engages with said first endplate;
a second surface that is opposite to said first surface and engages with said second endplate; and
wherein at least one of said first and the second endplates is locked to said spacer by advancing said spacer between said first and said second end plates and towards the posterior ends of said endplates until a flexible tab self-locks into a locking slot by resiliently biasing into said locking slot.

2. The spinal fusion device of claim 1, wherein said flexible tab is on said spacer and said locking slot is on said at least one endplate.

3. The spinal fusion device of claim 1, wherein said flexible tab is on said at least one endplate and said locking slot is on said spacer.

4. A spinal fusion device, comprising:
a first endplate configured for fitting within a disc space and engaging with a first vertebra, wherein said first endplate has an anterior end and a posterior end; and
a second endplate configured for fitting within said disc space and engaging with a second vertebra, wherein said second endplate has an anterior end and a posterior end,
wherein said endplates are separated by a single spacer that maintains a pre-determined distance between said endplates, said spacer comprising:
an anterior end;
a posterior end;
a first lateral side;
a second lateral side, opposite to said first lateral side;
a first surface that engages with said first endplate;
a second surface that is opposite to said first surface and engages with said second endplate; and
a locking device that releasably engages with said first and second endplates and allows in situ disassembly of said spacer from said fusion device after implantation, wherein said locking device comprises:
a first set of edges on said first surface of the spacer, said first set of edges engage with one or more slots on said first end plate;
a second set of edges on said second surface of said spacer, said second set of edges engage with one or more slots on said second end plate; and
one or more protrusions on said spacer that lock into one or more protrusion slots on one or both endplates, or one or more protrusions on one or both endplates that lock into one or more protrusion slots on said spacer,
wherein each protrusion comprises (1) a sloped front wall that allows said protrusion to be pushed into a protrusion slot by advancing the spacer between the first and the second end plates and towards the posterior ends of the endplates until said protrusion is resiliently biased into said protrusion slot and (2) a sloped back wall that allows said protrusion to be pulled out from said protrusion slot by retracting the spacer towards the anterior end of the end plates.

5. The spinal fusion device of claim 4, wherein said spacer comprises one or more protrusions on each of said first and second surfaces and said one or more protrusions lock into slots located on corresponding endplates.

6. The spinal fusion device of claim 4, wherein said first and second endplates each comprises one or more protrusions that lock into one or more protrusion slots located on said spacer.

7. The spinal fusion device of claim 4, wherein said sloped front wall of said protrusion forms a fixed angle of about 120 degree to about 170 degree with a surface that said protrusion is formed on and wherein said sloped back wall of said protrusion forms a fixed angle of about 95 degree to about 120 degree with said surface.

8. The spinal fusion device of claim 4, wherein said protrusion is formed on a cantilever to provide mobility in the direction perpendicular to a surface on which said protrusion is formed.

9. The spinal fusion device of claim 4, wherein said first set of edges on said first surface of the spacer comprises a first pair of edges located proximate to said first lateral side of said spacer and a second set of edges located proximate to said second lateral side of said spacer, and wherein said first endplate comprises a first dovetail slot that engages with said first pair of edges on said spacer and a second dovetail slot that engages with said second pair of edges on said spacer.

10. The spinal fusion device of claim 9, wherein said first endplate further comprises a third dovetail slot for engagement with an endplate inserter.

11. The spinal fusion device of claim 4, wherein said first set of edges on said first surface of the spacer comprises a first edge located proximate to said first lateral side of said spacer and a second edge located proximate to said second lateral side of said spacer, and wherein said first endplate comprises a dovetail slot that engages with said first and second edges of said spacer.

12. The spinal fusion device of claim 11, wherein said first endplate further comprises a second dovetail slot for engagement with an endplate inserter.

13. The spinal fusion device of claim 4, wherein said spacer comprises a first arm at said first lateral side and a second arm at said second lateral side, wherein said first and second arms are connected by a first cross bar at said posterior end of said spacer.

14. The spinal fusion device of claim 13, wherein said spacer further comprises a second cross bar at said anterior end of said spacer, and wherein said arms and cross bars define a cavity in said spacer.

15. The spinal fusion device of claim 14, wherein said second cross bar at said anterior end is removable to allow insertion of a bone graft into said cavity.

16. The spinal fusion device of claim 1, wherein said first endplate has a thickness at the anterior end and a thickness at the posterior end, and wherein the thickness at the anterior end is greater than the thickness at the posterior end, so as to maintain a desired lordotic angle between said first and second vertebrae.

17. The spinal fusion device of claim 16, wherein said second endplate has a thickness at the anterior end and a thickness at the posterior end, and wherein the thickness at the anterior end is greater than the thickness at the posterior end to form a plate lordotic angle that helps to maintain a desired lordotic angle between said first and second vertebrae.

18. The spinal fusion device of claim 17, wherein said first endplate and said second endplate have different plate lordotic angles.

19. The spinal fusion device of claim 4, wherein said spacer has an uneven thickness that maintain a desired lordotic angle between said first and second vertebrae.

20. A method for implanting the spinal fusion device in a subject, comprising:
- preparing a disc space between two adjacent vertebrae;
- inserting a pair of endplates into said disc space, wherein each endplate comprises an anterior end, a posterior end, a locking hole, and protrusions on an outer surface;
- inserting a spacer between said pair of endplates, wherein said spacer comprises an anterior end, a posterior end, a first surface that engages with said first endplate, a second surface that engages with said second endplate, a first flexible locking tab on said first surface, and a second flexible locking tab on said second surface;
- advancing said spacer between said pair of endplates towards the posterior end of said endplates until said locking tabs self-locks with corresponding locking holes on said first and second endplates by resiliently biasing into said locking holes.

* * * * *